(12) United States Patent
Wang et al.

(10) Patent No.: US 11,540,836 B2
(45) Date of Patent: Jan. 3, 2023

(54) LEFT ATRIAL APPENDAGE OCCLUDER FOR IMPROVING SEALING EFFECT AND MANUFACTURING METHOD THEREOF

(71) Applicant: HANGZHOU NUOMAO MEDTECH TECHNOLOGY CO., LTD., Zhejiang (CN)

(72) Inventors: Yongsheng Wang, Zhejiang (CN); Sievert Horst, Zhejiang (CN); Jianmin Li, Zhejiang (CN)

(73) Assignee: HANGZHOU DINOVA EP TECHNOLOGY CO., LTD.

( * ) Notice: Subject to any disclaimer, the term of this patent is extended or adjusted under 35 U.S.C. 154(b) by 138 days.

(21) Appl. No.: 16/693,007

(22) Filed: Nov. 22, 2019

(65) Prior Publication Data
US 2020/0085445 A1    Mar. 19, 2020

Related U.S. Application Data

(63) Continuation of application No. PCT/CN2018/087552, filed on May 18, 2018.

(30) Foreign Application Priority Data

May 23, 2017    (CN) .......................... 201710369080.1

(51) Int. Cl.
*A61B 17/12*    (2006.01)
*A61B 17/00*    (2006.01)

(52) U.S. Cl.
CPC .. *A61B 17/12122* (2013.01); *A61B 17/12031* (2013.01); *A61B 17/12172* (2013.01);
(Continued)

(58) Field of Classification Search
CPC .... A61B 17/12163; A61B 2017/00526; A61B 2017/00579; A61B 2017/00592; A61B 2017/00831; A61B 2017/00867; A61B 2017/1205; A61B 17/12172; A61B 17/12122; A61B 17/12031; A61B 2017/00243; A61B 2017/00597; A61B 2017/00632; A61B 2017/00955; A61B 17/12; A61B 17/12145
See application file for complete search history.

(56) References Cited

U.S. PATENT DOCUMENTS 9,295,472 B2 *    3/2016    Ottma ................ A61B 17/0057
11,253,261 B2 *    2/2022    Jayaraman ....... A61B 17/12168
(Continued)

OTHER PUBLICATIONS

Supplementary European Search Report issued in corresponding EP Application No. EP 18805444, dated Jan. 29, 2021.

*Primary Examiner* — Julian W Woo

(74) *Attorney, Agent, or Firm* — Dinsmore & Shohl LLP

(57) ABSTRACT

A left atrial appendage occluder for improving sealing effect and a manufacturing method thereof are provided. The left atrial appendage occluder includes a sealing portion and an anchoring portion coupled to the sealing portion. The sealing portion and the anchoring portion abut against each other. A tight connection between the sealing portion and the anchoring portion can be achieved by applying a pre-tightening force, such that the left atrial appendage occluder can be better attached to and occlude the left atrial appendage after being release.

20 Claims, 18 Drawing Sheets

(52) U.S. Cl.
CPC .......... *A61B 2017/00243* (2013.01); *A61B 2017/00597* (2013.01); *A61B 2017/00632* (2013.01); *A61B 2017/00955* (2013.01)

(56) References Cited

U.S. PATENT DOCUMENTS

| | | | |
|---|---|---|---|
| 2010/0324585 A1 | 12/2010 | Miles et al. | |
| 2010/0324588 A1* | 12/2010 | Miles | A61B 17/12177 606/198 |
| 2012/0172927 A1* | 7/2012 | Campbell | A61B 17/1215 606/213 |
| 2013/0296912 A1* | 11/2013 | Ottma | A61B 17/0057 606/191 |
| 2014/0257374 A1* | 9/2014 | Heisel | B21D 39/00 606/213 |
| 2015/0005810 A1* | 1/2015 | Center | A61F 2/01 606/200 |

* cited by examiner

LEFT ATRIAL APPENDAGE OCCLUDER FOR IMPROVING SEALING EFFECT AND MANUFACTURING METHOD THEREOF

CROSS-REFERENCE TO RELATED APPLICATION(S)

This application is a continuation of PCT Application No. PCT/CN2018/087552, filed on May 18, 2018, which claims priority to Chinese Patent Application No. 201710369080.1, filed on May 23, 2017, the disclosures of which are hereby incorporated by reference in their entireties.

TECHNICAL FIELD

The present disclosure relates to the field of medical instruments, and in particular to an interventional treatment instrument for occluding a left atrial appendage (LAA) and a manufacturing method thereof.

BACKGROUND

Atrial fibrillation (AF) is the most common persistent arrhythmia. The incidence of AF increases with age and is up to 10% in people over 75 years old. When AF occurs, the atrial pulsation rate is up to 300-600 beats per minute. The heart rate is often fast and irregular, and an effective atrial systolic function is lost. In case of AF, the contractility of a left atrial appendage (LAA) is decreased; in addition, morphological characteristics of the LAA and the uneven trabecula in the LAA which make the blood flow generate an eddy in the LAA and the blood flow rate slow down, thus resulting in the formation of thrombus. For patients with nonvalvular AF, more than 90% of left atrium thrombi occur in the LAA, and after the thrombi fall off, the thrombi will enter the cerebral arterial blood vessels through the aorta, thereby causing cerebral embolism, namely stroke.

Currently, to prevent AF patients from the risk of stroke, preventive treatments are clinically performed by mainly utilizing the following three methods: anticoagulant treatment, surgical treatment, and percutaneous left atrial appendage occlusion (LAAO) treatment. The anticoagulant treatment is to restrain blood coagulation by oral anticoagulants, so as to reduce the risk of thrombus formation in the LAA, and then reduce the occurrence probability of stoke. Clinic trials show that the anticoagulant treatment can remarkably reduce the occurrence probability of stroke, but the anticoagulant treatment is a long-term process and also has remarkable complications, mainly including bleeding complications, and even may lead to severe cases. The surgical treatment includes surgical ablation or suture of LAA. However, surgical trauma is large, and such surgery is generally performed during the valve replacement surgery or the coronary artery bypass graft surgery. Patients, especially elderly patients, generally are hard to accept a simple LAA surgery. The percutaneous LAAO treatment is to deliver and then release a LAA occluder to the LAA disposed in the right atrium of the heart by utilizing a delivery sheath with a smaller diameter in a percutaneous puncture mode. The LAA occluder can occlude the orifice of the LAA to prevent blood flow in the atrium from entering the LAA, thereby preventing thrombus formation and achieving a purpose of preventing AF-induced thromboembolism. Since 2001, the percutaneous LAAO treatment has been in use, and has successively subject to animal experiments and clinical trials. Based on the clinical trials, the LAAO treatment can effectively reduce the occurrence probability of stroke of the AF patients.

The LAA occluder currently in the market mainly has two types of structures: a plug structure and a double-disc structure.

Because the application time of the LAA occluder is relatively short, the technology is relatively immature, there will be some complications after surgery and affect the living quality of the patient. Among them, residual shunt of an instrument is one of the main complications of LAA occlusion. In the case of the LAA occluder with the plug structure, 8% of patients had residual shunt complications from their 6-month follow-up results, and 32% to 34.5% of patients in different centers had some degrees of residual shunt complications from their 12-month follow-up results. In the case of the LAA occluder with the double-disc structure, 2%-16.2% of patients in different centers had moderate residual shunt complications from their 12-month follow-up results. The incidence of residual shunt complications is high, which will affect the living quality of patients. Therefore, reducing the residual shunt after LAA occlusion is one of the main goals of improving the clinical application value of the LAA occluder.

The LAA occluder with the double-disc structure usually includes a sealing portion and an anchoring portion. After the LAA occluder is released, the sealing portion occludes the orifice of the LAA, and the anchoring portion is released inside the LAA and is provided with barbs to fix the sealing portion. After being released, the sealing portion of the LAA occluder should be closely attached to the orifice of the LAA to occlude the LAA. If the sealing portion fails to be closely attached to the orifice of the LAA and the sealing portion may be suspended in the left atrium, resulting that a sufficient occlusion effect for the orifice of the LAA cannot be achieved, and the risk of thrombosis may be further increased. A major factor that causes the sealing portion to be ineffectively attached to the LAA is related to the connection between the sealing portion and the anchoring portion. That is, the anchoring portion and the sealing portion fail to be tightly connected together, the overall length of the occluder is relatively longer, and the anchoring portion is radially compressed, further increasing the overall length of LAA occlude after being released, and also causing an increase in the axial distance between the sealing portion and the anchoring portion, such that the sealing portion cannot be effectively attached to the LAA after being released, resulting in residual shunts.

SUMMARY

A left atrial appendage occluder is provided, which advances a connection manner between a sealing portion and an anchoring portion, thereby avoiding and inhibiting an axial elongation of the left atrial appendage occluder as a whole, and further ensuring that the sealing portion is attached to and occludes the left atrial appendage.

A left atrial appendage occluder for improving sealing effect includes a sealing portion and an anchoring portion coupled to the sealing portion. The sealing portion and the anchoring portion are in mutual abutment.

It is noted that the mutual abutment between the sealing portion and the anchoring portion refers to that at least a part of the sealing portion and at least a part of the anchoring portion are in contact with each other, and the sealing portion is deformed due to an abutment force.

According to the present disclosure, a tight connection between the sealing portion and the anchoring portion can be achieved by applying a pre-tightening force. After being released, the left atrial appendage occluder can be better attached to and occlude the left atrial appendage, and even if one of the anchoring portion and the sealing portion is radially compressed to lengthen, the sealing portion can be kept in contact with the anchoring portion to ensure the sealing effect.

The left atrial appendage occluder according to the present disclosure is capable of effectively improving the sealing performance and reducing residual shunts.

In combination with the related art, one or more layers of flow blocking membrane are disposed inside the sealing portion. A periphery of the anchoring portion can also be coated with a flow blocking membrane, for example, all or part of an outer surface of the anchoring portion is coated with the flow blocking membrane.

Unless otherwise stated, shapes and positional relationships herein are described based on a state in which the left atrial appendage occluder is released and expanded in a body, and the state may also be referred to be a released state or an expanded state. Before being released, the left atrial appendage occluder is compressed within a delivery device to be in a state which may be referred to be a compressed state or a pre-release state.

In an embodiment, the sealing portion and the anchoring portion separately and independently have a wire frame structure or a mesh-shaped structure.

The sealing portion and the anchoring portion can be processed by weaving or cutting, individually. The sealing portion (or the anchoring portion) can be in a regular or irregular wire frame structure. The sealing portion in the wire frame structure may be provided with a framework, as required, at a suitable position in the wire frame structure to increase a strength, and the framework may have a larger cross-sectional area or have at least a greater strength with respect to other portions of the sealing portion. The sealing portion in the network-shaped structure may include regular or irregular cells, and in an implementation, the network-shaped structure includes diamond-shaped cells or substantially diamond-shaped cells. The network-shaped structure is at least radially compressible to facilitate retraction and release. The mesh-shaped structure explicitly appears a warp and weft structure, and longitudinal parts and latitudinal parts of the mesh-shaped structure intersect with each other via nodes in a fixed manner. In an implementation, the longitudinal parts and the latitudinal parts of the mesh-shaped structure intersect with each other in a non-fixed manner, that is, the longitudinal parts and the latitudinal parts can be slidably moved with respect to each other in an intersecting manner, thereby providing a capability of compliance and deformation.

In an embodiment, the sealing portion is a sealing disc or a sealing plug.

It is noted that the term "disc" or "plug" is used to represent a general shape. For example, the term "disc" represents a structure in a flat shape with an outer edge, and the outer edge is in a shape, such as a circular shape or other shapes according to actual requirements, substantially fitted with features of anatomical structures of the left atrial appendage.

For example, the term "plug" is used to represent a structure in a column shape with a certain thickness, such as an approximate cylinder and cone. However, a shape of an outer circumference or a generatrix of the sealing portion is not strictly limited, and can be defined referring to the related art on one hand and the actual requirements on the other hand. The shape of the sealing portion itself is not critical to the present disclosure. But of course, the present disclosure provides a preferred or improved solution for the sealing portion.

In an embodiment, the sealing portion is a sealing disc. The sealing portion is provided with a presetting state and an abutting state. In the presetting state, the sealing portion is free from contact with the anchoring portion. In the abutting state, the sealing portion is in contact with the anchoring portion. A middle part of a disc bottom of the sealing portion in the abutting state is deformed facing axially toward the anchoring portion with respect to the presetting state.

In an embodiment, the middle part of the disc bottom of the sealing portion in the abutting state is provided with a deformation protruding axially toward the anchoring portion with respect to the presetting state.

In an embodiment, the sealing portion includes a disc surface facing away from the anchoring portion, a disc bottom facing the anchoring portion, and an intermediate part connecting the disc surface and the disc bottom. The disc bottom is planar, or a middle part of the disc bottom protrudes toward the anchoring portion, or the middle part of the disc bottom protrudes away from the anchoring portion.

The disc surface, the disc bottom, and the intermediate part integrally form a cage-shaped structure. One or more flow blocking membranes may be disposed inside the cage-shaped structure. Parts of the cage-shaped structure other than necessary hollow parts may be closed or partially open. When weaving and processing the sealing portion, one converging end may be formed at each of the disc bottom and the disc surface.

Since the cage-shaped structure has a certain space inside, the sealing effect can be ensured even if there is a certain deformation in the cage-shaped structure. According to the present disclosure, the cage-shaped structure is particularly suitable for achieving a tight abutment against the anchoring portion.

A diameter of the cage-shaped structure mainly includes a diameter of the intermediate part, a diameter of the anchoring portion, and a diameter of the disc surface. The diameter of the intermediate part is substantially equal to the diameter of the anchoring portion. The diameter of the disc surface is slightly larger than the diameter of the intermediate part, so as to improve the sealing effect of an end of the sealing portion.

In an embodiment, the sealing portion is provided with a presetting state and an abutting state. In the presetting state, the sealing portion is free from contact with the anchoring portion. In the abutting state, the sealing portion is in contact with the anchoring portion. A diameter of the disc bottom in the presetting state is larger than a diameter of the disc bottom in the abutting state.

The disc surface or the disc bottom described herein may be in an approximately circular shape. If the disc surface or the disc bottom is in other shapes, it may be appreciated that a cross-sectional area or an overall thickness of the disc bottom in the presetting state is larger than that of the disc bottom in the abutting state. Taking the disc surface and the disc bottom in a circular shape as an example, since a diameter of the disc surface is larger than a diameter of the disc bottom, the sealing portion is in a truncated cone shape as a whole. The sealing portion is progressively converged as it goes toward a bottom end thereof, such that a top surface of an upper end of the sealing portion is slightly larger, and a bottom surface of the bottom end of the sealing portion is slightly smaller. In this way, when the sealing portion is in contact with the anchoring portion, the sealing portion can be conformed to be attached with the anchoring portion.

In an implementation, the sealing portion is provided with a presetting state and an abutting state. In the presetting state, the sealing portion is free from contact with the anchoring portion. In the abutting state, the sealing portion is in contact with the anchoring portion. At least one of the intermediate part and the disc bottom of the sealing portion in the abutting state has a deformation with respect to the presetting state.

The presetting state refers to a state in which a shape of the sealing portion after being processed but before assembling the left atrial appendage occluder or subjecting the sealing portion to an external force. After assembly, since the sealing portion is in abutment against the anchoring portion, and in order to increase or maintain the pre-tightening force between the sealing portion and the anchoring portion, the sealing portion is deformed after being abutted against the anchoring portion.

In an embodiment, the intermediate part of the sealing portion in the abutting state has a radially contracted deformation with respect to the presetting state.

When the sealing portion and the anchoring portion are moved away from each other or subjected to a radially compression, the radially contracted deformation can offset or delay a tendency of an axial elongation of the left atrial appendage occluder to ensure a sealing for an opening portion of the left atrial appendage. The radially contracted deformation allows the intermediate part to have a certain taper and to better fit the left atrial appendage, so as to improve the sealing effect.

In an embodiment, the disc bottom of the sealing portion in the abutting state is provided with a deformation protruding axially toward the anchoring portion with respect to the presetting state.

Based on a similar principle, the deformation protruding axially toward the anchoring portion can also offset or delay the axial elongation as a whole. The abutment between the sealing portion and the anchoring portion is substantially maintained to ensure the sealing effect.

In an embodiment, the sealing portion abuts against the anchoring portion at least at an outer edge of the disc bottom. The outer edge of the disc bottom is abutted against the anchoring portion, and a greater deformation of the sealing portion can be obtained under a same pre-tightening force, which is more favorable for compensating and offsetting the axial elongation.

In an embodiment, connection parts of the sealing portion and the anchoring portion are connected in a staggered manner.

In an embodiment, the sealing portion and the anchoring portion are constricted and converged respectively, and the sealing portion and the anchoring portion are connected together via a connector.

In the present disclosure, wire strands of the sealing portion and the anchoring portion can be connection parts formed by shape convergence. The connection parts of the sealing portion and the anchoring portion extend toward each other and are fixed in a staggered manner.

However, the connection parts formed by shape convergence are not limited to be formed in a converged manner. In the related art, the connection parts of the sealing portion and the sealing portion are generally aligned with each other, and end surfaces of the connection parts are directly abutted against each other when the connection parts are directly connected. Of course, a transitional connector can also be adopted, but this structure will lead to an excessive overall axial length of the left atrial appendage occluder, which is disadvantageous for sealing.

In the present disclosure, the connection parts of the sealing portion and the anchoring portion are connected in a staggered manner, such that the connection parts can extend toward each other without spatially interference, a distance between the sealing portion and the sealing portion can be greatly reduced, and the sealing effect can be improved.

In an embodiment, both of the sealing portion 1100 and the anchoring portion 1200 are integrated with or fixed to their connection part respectively.

The sealing portion and the anchoring portion may be integrated with their respective connection parts after a laser cutting or weaving process. Alternatively, the connection parts are independent members and are fixed with sealing portion and the anchoring portion respectively by welding or the like. In an implementation, the sealing portion and the anchoring portion are integrated with their respective connection parts, thereby facilitating processing and ensuring overall strength.

In an embodiment, the above-mentioned shape convergence is a global convergence or a local convergence.

As the sealing portion and the anchoring portion are used to occlude the left atrial appendage, parts of the sealing portion and the anchoring portion have various diameters ranged within a certain size range, while diameters of the connection parts are smaller. Thus the transition in diameter between a main body of the sealing portion and the connection part of the sealing portion, and a transition in diameter between a main body of the anchoring portion and the connection part of anchoring portion, are gradual or abrupt. For example, when the connection parts are converged in a manner of global convergence, a portion with a varied diameter is in a tapered structure. The local convergence can be considered as an abrupt change in diameter, for example, a portion with a larger cross-sectional area abruptly changes into a rod or a strand with a smaller cross-sectional area.

In an embodiment, each of the sealing portion and the anchoring portion has one connection part connected with the other. Alternatively, each of the sealing portion and the anchoring portion has multiple connection parts, and the multiple connection parts of the sealing portion are connected with the multiple connection parts of the anchoring portion in a one-to-one correspondence.

The number and positions of the connection parts are not strictly limited. In a case that each of the sealing portion and the anchoring portion has only one connection part, the connection part is generally arranged in a middle of the sealing portion or the anchoring portion.

In an embodiment, the connection parts of the sealing portion and anchoring portion are directly connected or connected via a connector.

When the connection parts are directly connected, that is, the connection parts of the sealing portion and anchoring portion are in contact with each other, and are fixed to each other by welding, hooping, intertwining, and the like. When the connection parts are connected via a connector, that is, the connection parts may be free from contact with each other, but are respectively fixed with the connector, and the connector may be a single component or an assembly of multiple components.

In an embodiment, each of the connection parts of the sealing portion and the anchoring portion extends along a straight line.

Alternatively, one of the connection parts extends along a straight line and the other of the connection parts extends along a curve line.

Alternatively, each of the connection parts of the sealing portion and the anchoring portion extends along a curve line.

The sealing portion and the anchoring portion are arranged oppositely, and the connection parts of the sealing portion and the anchoring portion extend toward and are connected with each other, and the paths along which the connection parts extend are not strictly restricted during an extending process. In order to simplify the structure, in an implementation, each of the connection parts of the sealing portion and the anchoring portion extends along a straight line.

The connection part itself may be either a simple straight rod or a relatively complicated three-dimensional structure, and thus extending along a straight line herein should be understood as an overall trend, that is, the extending process does not involve with a circuitous or bending shape as a whole.

Further, in an embodiment, the connection parts of the sealing portion and the anchoring portion both extend along an axial of the left atrial appendage occluder.

In an embodiment, the connection parts of the sealing portion and the anchoring portion are nested within or offset with each other at a position in which the sealing portion and the anchoring portion cooperate with each other.

Since the connection parts of the sealing portion and the anchoring portion are arranged in a staggered manner, the connection parts can extend to be staggered with each other in a mutually nested manner or in a mutually offset manner without spatial interference. A mutually offset manner is defined with respect to the mutually nested manner, and should not be understood as being far away from each other. For example, in a cross section perpendicular to the axial of the left atrial appendage occluder, the connection parts of the sealing portion and the anchoring portion may be attached to each other or have a certain gap therebetween.

In an embodiment, the connection parts of the sealing portion and the anchoring portion extend toward each other, and each of the connection parts extends beyond a terminal end of the other connection part.

When one connection part extends beyond the terminal end of the other connection part, it also means that the terminal end of the other connection part extends beyond a terminal end of the one connection part. In this way, the connection parts have projections, in a direction perpendicular to the axial of the left atrial appendage occluder, arranged side by side or at least partially overlap with each other at a position in which the connection parts of the sealing portion and the anchoring portion cooperate with each other.

When one of the sealing portion and the anchoring portion is nested within the other, the projections of the sealing portion and the anchoring portion must overlap. When the sealing portion and the anchoring portion are offset with each other, the shapes of the projections of the sealing portion and the anchoring portion are related to a projection direction, and it is possible that the projections of the sealing portion and the anchoring portion are arranged side by side or partially overlap with each other. When the sealing portion and the anchoring portion are offset with each other and one of the sealing portion and the anchoring portion does not extend beyond a terminal end of the other, the sealing portion and the anchoring portion can be further moved toward each other and the structure of the left atrial appendage occluder is not compact enough.

In the case that the sealing portion and the anchoring portion each have mesh-shaped structures, wires for weaving the sealing portion and the anchoring portion are bundled individually and further connected with each other via a connector. Structure features is formed by bundling the wires, corresponding steps in the processing are included in the process of bundling, and that is, multiple wires are converged and bundled into one strand.

In the case that the sealing portion and the anchoring portion each have wire frame structures, the sealing portion or the anchoring portion is generally formed by cutting a pipe, and an end terminal of the pipe can be considered as a converging part.

In an embodiment, the sealing portion includes a bottom part facing the anchoring portion, and the bottom part of the sealing portion includes a first converging part. A middle part of the anchoring portion in a radial direction includes a second converging part. The first converging part and the second converging part extend toward each other and are misaligned.

Pulling the first converging and the second converging toward the connector in opposite directions may cause the main bodies of the sealing portion and the anchoring portion to be moved close to and until tightly abutted against each other. The first converging and the second converging are pulled through separate channels, thereby avoiding interference and facilitating assembly.

In an embodiment, the first converging part and the second converging part are arranged side-by-side in a staggered manner or are arranged in a nesting inside and outside in a staggered manner. In general, two channels are arranged offset from each other, thereby further avoiding interference during pulling the first converging part and the second converging part and facilitating assembly.

In an embodiment, the anchoring portion extends from the connector away from the sealing portion to form an extending portion. One side of the extending portion facing away from the connector is bent outward and turns back to the bottom part of the sealing portion to form a turning-back portion. The turning-back portion is abutted against the bottom part of the sealing portion.

The anchoring portion is an outward bent structure as a whole. The turning-back portion extends around a periphery of the extending portion, such that the turning-back portion and the extending portion together form a double-layer structure. A certain space is defined inside the double-layer structure, which can accommodate and allow a deformation of the anchoring portion, after the anchoring portion is tightly abutted against the sealing portion, without weakening the anchoring effect.

In an embodiment, the anchoring portion extends from the connector away from the sealing portion to form an extending portion. One side of the extending portion facing away from the connector is bent outward and turns back to the bottom part of the sealing portion to form a turning-back portion. The turning-back portion bends inward and is constricted at the bottom part of the sealing portion to form a necked opening portion. The necked opening portion abuts against the bottom part of the sealing portion.

The turning-back portion bends inward and is constricted at the bottom part of the sealing portion to form the necked opening portion, and the necked opening portion abuts against the bottom part of the sealing portion.

The necked opening portion extends inward substantially and radially to be in surface contact with the bottom part of the sealing portion, thereby facilitating applying a pre-tightening force. Although the anchoring portion and the sealing portion are in hollow structures, the surface contact herein can be understood as an abutment between mesh-shaped surfaces, and it is not necessary to be limited to a surface contact between solid bodies.

In an embodiment, the first converging part is disposed at a center of the bottom part of the sealing portion. The necked opening portion extends upward to abut against an outer edge of the bottom part of the sealing portion. In this way, the bottom part of the sealing portion is formed into an inverted cone shape under the action of the pre-tightening force.

In an embodiment, the necked opening portion is suspended above a periphery of the extending portion or connected to the extending portion. When the necked opening portion is suspended above the periphery of the extending portion, that is, the necked opening portion and the periphery of the extending portion are not connected or only slightly contact with each other, and are freely movable relative to each other when deformed. When the necked opening portion is connected to the extending portion with one of a fixed connection, a sliding connection, and a rotation fit, a relative movement between the necked opening portion and extending portion is restrained in some extent.

In an embodiment, the extending portion is in a tapered shape, and an end of the extending portion having a larger diameter is disposed away from the connector and is provided with an opening.

The extending portion is in a horn-shaped structure, thereby facilitating retraction and improving strength and structural stability at a flared end (that is, the end of the extending portion provided with the opening).

In an embodiment, the anchoring portion is provided with a presetting state and an abutting state. In the presetting state, the anchoring portion is free from contact with the sealing portion. In the abutting state, the anchoring portion is in contact with the sealing portion. The connector is farther away from the sealing portion than the necked opening portion along an axial direction of the anchoring portion in the presetting state.

That is, when the sealing portion is moved toward the anchoring portion, the necked opening portion comes in contact with the bottom part of the sealing portion first, and meanwhile, the connector is still at a distance from the sealing portion, and this distance also allows a further pulling to form the pre-tightening force.

In an embodiment, the connector is flush with the necked opening portion or farther away from the sealing portion than the necked opening portion along the axial direction of the anchoring portion in the abutting state.

In an embodiment, the connector includes an outer ring and an inner ring nested within the outer ring. One of the first converging part and the second converging part extends through and is fixed in the inner ring, and the other one of the first converging part and the second converging part extends through and is fixed in a gap between the inner ring and the outer ring.

In an embodiment, the connector includes an outer ring and an inner ring nested within the outer ring. One of the first converging part and the second converging part extends through and is fixed in a gap between the inner ring and the outer ring, and the other one of the first converging part and the second converging part penetrates through the inner ring and is provided with a retainer abutted against the connector. The retainer is fixed to one end of the inner ring where the other one of the first converging part and the second converging part extends out.

In an embodiment, the connector includes a body having two passages arranged side by side. The first converging part and the second converging part extend through the two passages respectively and are provided with two retainers abutted against respective sides of the passages where which the first converging part and the second converging part extend out correspondingly.

The connector and the retainer may be stainless steel, nickel titanium alloy, or other metal material that meets biocompatibility requirements.

In an embodiment, the anchoring portion has an abutting portion that abuts against the sealing portion. In a compressed state, the anchoring portion is in a cylindrical structure, and the abutting portion is on an inner wall of the cylindrical structure.

In an embodiment, the anchoring portion in a compressed state is in a cylindrical structure, and an inner wall of the cylindrical structure in a released state abuts against the sealing portion.

When the left atrial appendage occluder is released, the anchoring portion bends outward, such that the abutting portion originally located on the inner wall of the cylindrical structure bends to be outside and faces the sealing portion, and the abutting portion is further tightly abutted against the sealing portion.

In the compressed state, if the abutting portion is on the outer wall of the cylindrical structure, the anchoring portion needs to bend in a more complicated manner, otherwise it is difficult for the anchoring portion to achieve a larger outer diameter to support and anchor at an inner wall of the left atrial appendage.

However, when the anchoring portion is to be bent in a complicated manner, the tendency of extending outward of an end terminal of the anchoring portion (i.e., a distal end of the anchoring portion in the compressed state) can be changed, and the inner wall of the left atrial appendage can be prevented from being stabbed, thereby improving the safety.

In an embodiment, the anchoring portion and the sealing portion are directly connected and abutted against each other in a using state.

In a normal using state, the anchoring portion may be in direct contact with and abutted against the sealing portion. However, during using, the anchoring portion and the sealing portion are not always in the state of directly contacting with and abutting against each other. Under the action of a special anatomical structure or after being used for a period of time, the anchoring portion and the sealing portion may also be moved away from each other and even bring a gap created between the anchoring portion and the sealing portion.

In an embodiment, the sealing portion is a two-layer structure. The two-layer structure includes a bottom layer facing the anchoring portion and a top layer facing away from the anchoring portion. The sealing portion is connected to the anchoring portion through the bottom layer.

Alternatively, a part of the anchoring portion extends through the sealing portion to connect with the top layer of the sealing portion. In the present disclosure, the anchoring portion is connected to the bottom part of the sealing portion, it is favorable for obtaining a pre-deformation or a higher deformation efficiency of the sealing portion when the anchoring portion and the sealing portion are mutually abutted.

In an embodiment, one or more layers of flow blocking membrane are provided inside the two-layer structure.

Since a sealing portion with a two-layer structure is more likely to be loose and elongated axially, the present disclosure is also preferably applicable to a sealing portion with a two-layer structure. Both a sealing portion in a disc shape and in a column shape can be regarded as a two-layer structure with a flow blocking membrane provided inside.

In an embodiment, the sealing portion and the anchoring portion are formed individually and abut against each other during an assembling process.

The sealing portion and the anchoring portion are formed separately and thermoformed individually and then are assembled together. During assembly, a pre-deformation effect can be obtained by causing the sealing portion and the anchoring portion abutted against each other tightly. If the sealing portion and the anchoring portion are formed in an integrated structure, an abutting effect can also be obtained. However, since the sealing portion and the anchoring portion are formed integrally rather than assembled together, it is necessary to obtain the abutting effect after thermoforming, resulting in higher requirements for a thermoforming technic, and it is required that the sealing portion and the anchoring portion are separately thermoformed, thereby increasing the processing difficulty.

In order to obtain a better effect of support and anchoring, the anchoring portions are deployed continuously circumferentially.

Although a mesh-like or a rod-like structure has some gaps along the axial direction, it should be continuously extended in the axial direction in terms of the overall structure and distribution, in order to obtain a more uniform force distribution and stable support, and to avoid providing support merely by circumferentially local structure.

In an embodiment, a part of the anchoring portion abutted against the sealing portion is adjacent to an outer edge of the anchoring portion.

In an embodiment, a part of the sealing portion abutted against the anchoring portion is adjacent to an outer edge of the sealing portion.

The outer edges of the sealing portion and the anchoring portion abutting against each other facilitates an axial deformation or a radially convergence, and increasing deformation quantity under a same force.

In an embodiment, after thermoforming, the sealing portion and the anchoring portion are assembled together, and the sealing portion and the anchoring portion are in a first state in an initial contact with each other during assembly, and connection parts of the sealing portion and the anchoring portion are in a second state after axially moving a predetermined distance toward each other.

In the first state, the sealing portion and the anchoring portion have been and are just in contact with each other. Since both the sealing portion and the anchoring portion have been thermoformed, and when they are further axially moved toward each other, one of them will deform and maintain a stress caused by the deformation in the second state.

In an embodiment, the connection parts of the sealing portion and the anchoring portion are respectively disposed at middle parts of the sealing portion and the anchoring portion in a radial direction. In the first state, the sealing portion and the anchoring portion are in contact with each other at peripheral regions around the connection parts respectively.

The pre-tightening force is also derived from the above-mentioned stress. If the thermoforming is performed after assembly rather than before assembly, the stress will disappear during the thermoforming and the pre-tightening force required cannot be created.

Therefore, it is noted that, in the second state, a relative positional relationship between the sealing portion and the anchoring portion is obtained after assembly, and the thermoforming is not performed after the second state.

Since the anchoring portion has greater stiffness, and generally, the stress is mainly generated from the deformation of the sealing portion.

In an embodiment, in the second state a part of the sealing portion connected with the anchoring portion moved towards the anchoring portion with respect to the first state.

In the second state, a distance in which the connection parts of the sealing portion and the anchoring portion axially move toward each other affects a magnitude of the stress, and therefore, it is necessary to define and control the distance in an adaptive manner during assembly.

In an embodiment, the predetermined distance is defined according to one of: an axial force of the connection parts between the sealing portion and the anchoring portion, a pressing force at contacting parts of the sealing portion and the anchoring portion, and a deformation of the part of the sealing portion connected with the anchoring portion.

In an embodiment, the deformation is an axial displacement of a predetermined part of the sealing portion, or an angle between the predetermined part of the sealing portion and an axis of the sealing portion.

The predetermined part of the sealing portion is a part that is deformed from the first state to the second state. For ease of expression and measurement, a part with a larger deformation can be selected as the predetermined part. For example, the predetermined part of the sealing portion is a part of the sealing portion in contact with the anchoring portion in the first state.

During assembly, the magnitude of the stress can be obtained by detecting variations of the predetermined distance.

If it fails to provide such stress, even if there is a local contact between the sealing portion and the anchoring portion during assembly, when the left atrial appendage occluder is axially elongated as a whole during use (that is, the sealing portion and the anchoring portion are away from each other), an inherent recovery force between the sealing portion and the anchoring portion is smaller, an overall axial elongation of the left atrial appendage occluder is counteracted merely by the elasticity of the respective materials.

The left atrial appendage occluder according to the present disclosure is first thermoformed and then is assembled by retaining an axial stress, the overall axial elongation of the left atrial appendage occluder in a subsequent use process can be better counteracted. The recovery force is increased by superposing the pre-tightening force and resilient forces of the sealing portion and the anchoring portion, thereby ensuring the sealing effect for long-term use.

A method for manufacturing a left atrial appendage occluder is also provided. The method is carried out as following. Thermoforming is performed on a sealing portion and an anchoring portion. When assembling the sealing portion with the anchoring portion, the sealing portion and the anchoring portion is moved toward each other to reach a first state, and in the first state the sealing portion and the anchoring portion are in initial contact with each other. The sealing portion and the anchoring portion is further moved axially toward each other a predetermined distance to reach a second state. And then, connection parts of the sealing portion and the anchoring portion are fixed together, the connection parts are maintained in the second state to complete assembly.

Since the sealing portion and the anchoring portion have been in partial contact with each other in the first state, and therefore, when the left atrial appendage occluder is transformed into the second state from the first state, an axial distance between the overall sealing portion and the anchoring portion is not changed, only a stress generated from local deformations is changed.

A method for manufacturing a left atrial appendage occluder for improving sealing effect is also provided. The method includes manufacturing a sealing portion and an anchoring portion, and causing the sealing portion to be tightly connected with and abutted against the anchoring portion.

The left atrial appendage occluder according to the present disclosure is delivered to the left atrial appendage of the heart by utilizing a delivery sheath in a percutaneous puncture mode, so as to block the left atrial appendage and to avoiding a risk of a stroke in patients with atrial fibrillation due to thrombus formation in the left atrial appendage.

A tight connection between the sealing portion and the anchoring portion is realized by an improved connection manner according to the present disclosure, and a certain pre-tightening force is maintained to allow the sealing portion to be tightly attached to the left atrial appendage to occlude an orifice of the left atrial appendage, thereby reducing the incidence of endoleaks and residual shunts.

Figure 12A:
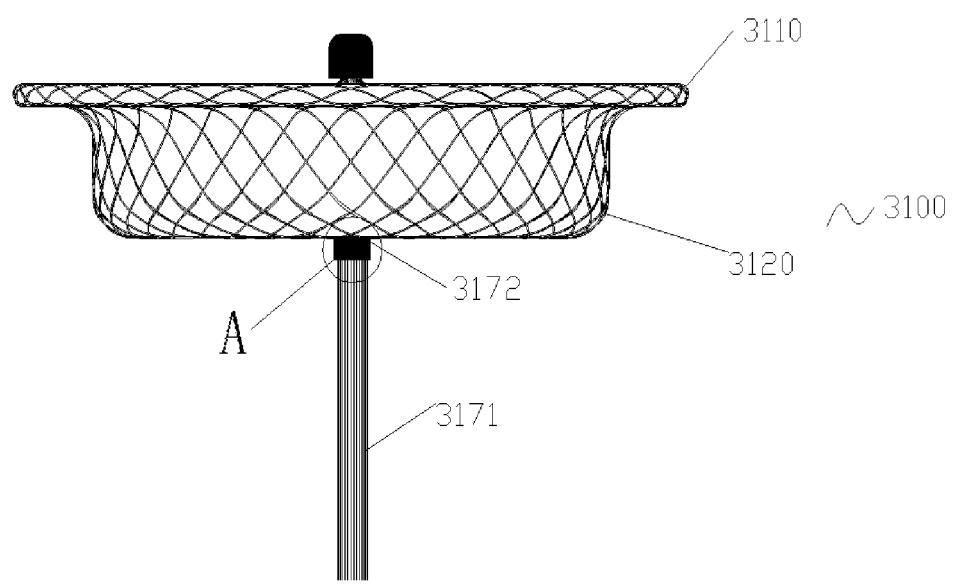
FIG. 12A is a schematic view illustrating a process of connecting the anchoring portion and the sealing portion according to a third embodiment.
Figure 13:
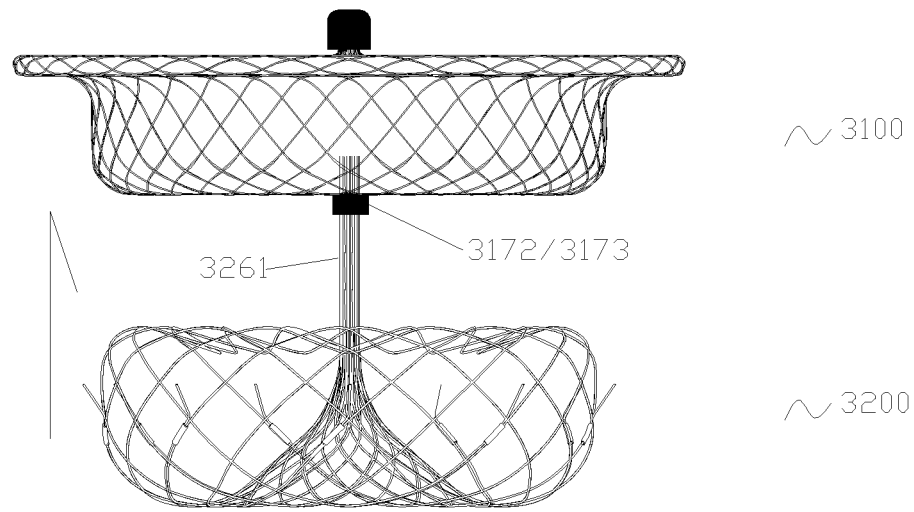
Figure 14:
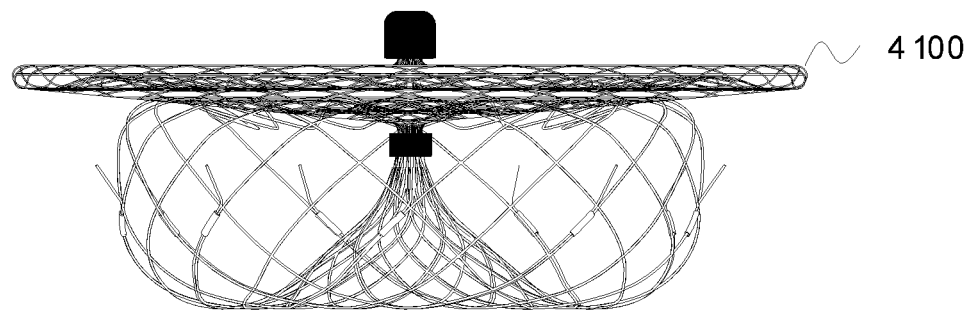
Figure 15:
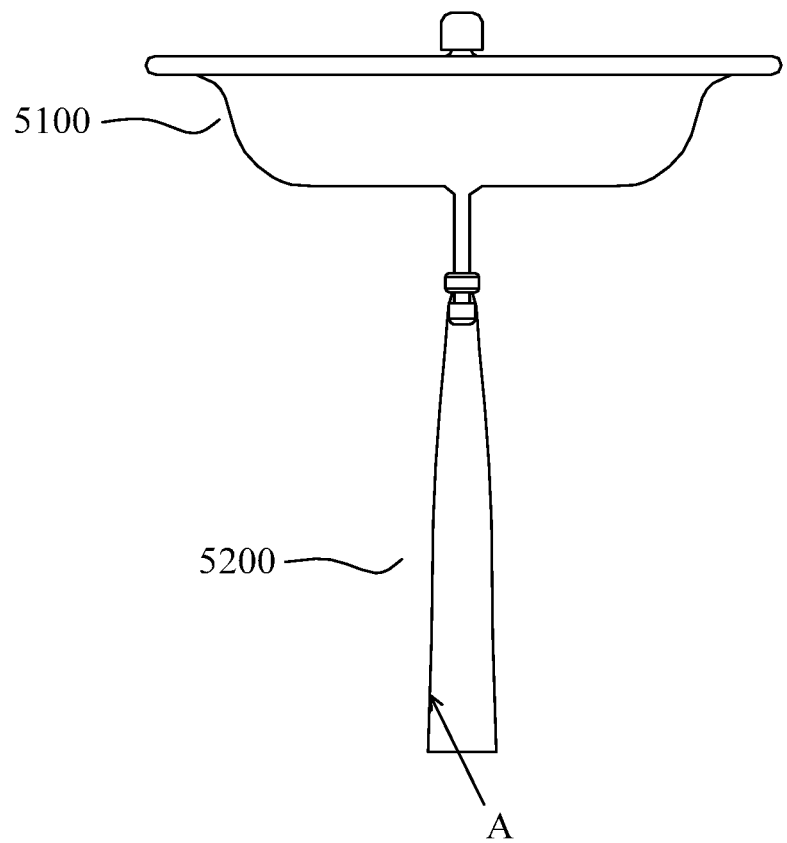
Figure 16:
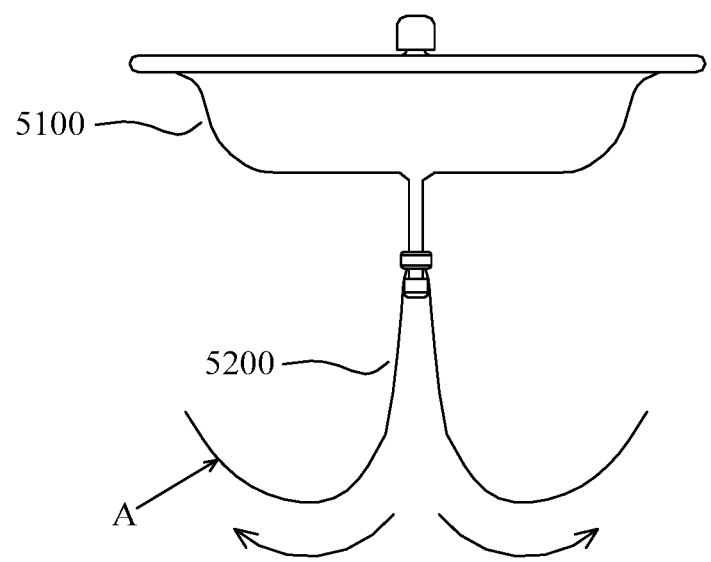
Figure 17:
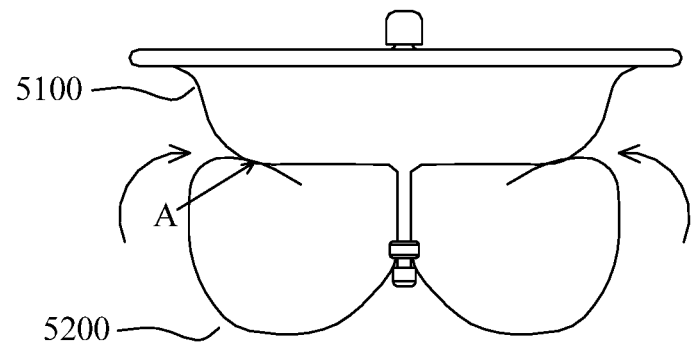
Figure 18:
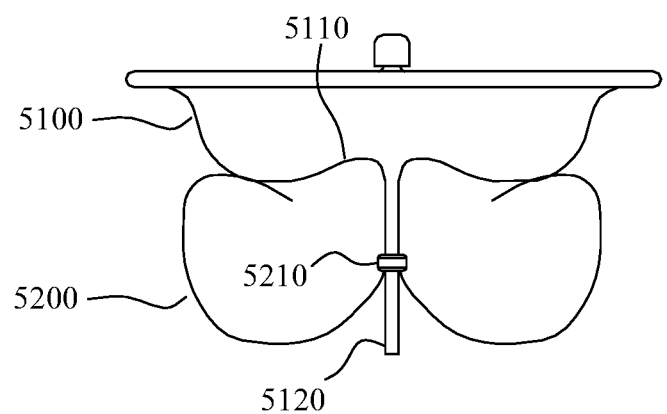
Figure 19:
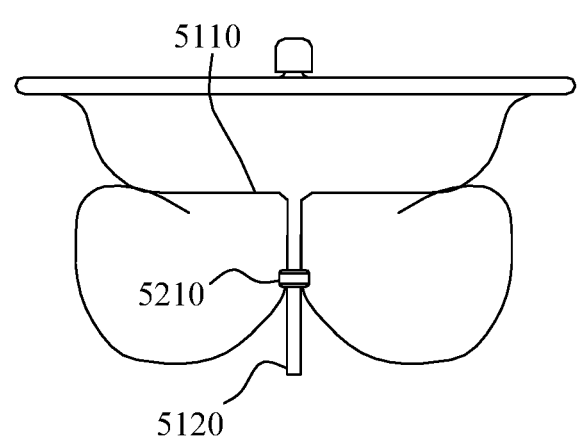
Figure 20:
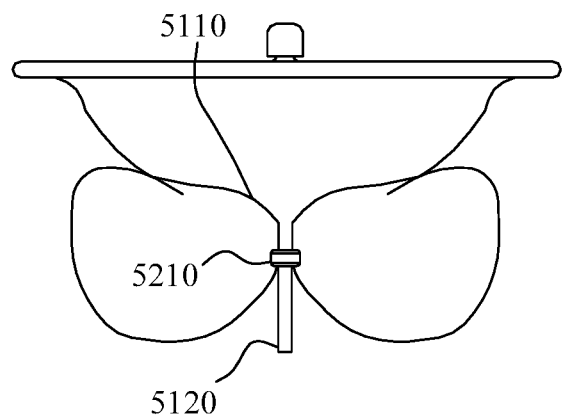
Figure 21:
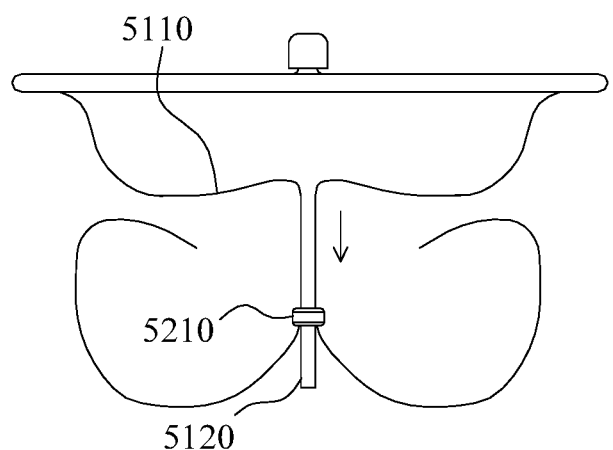
Figure 26:
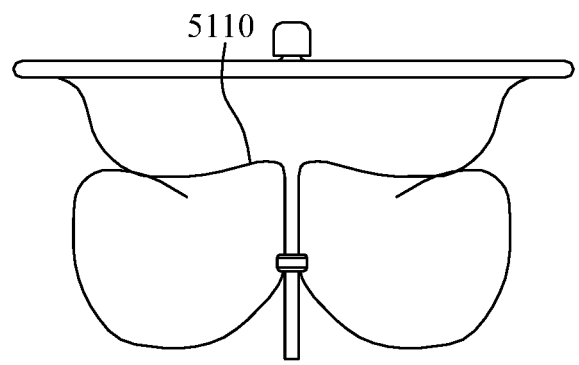
Figure 27:
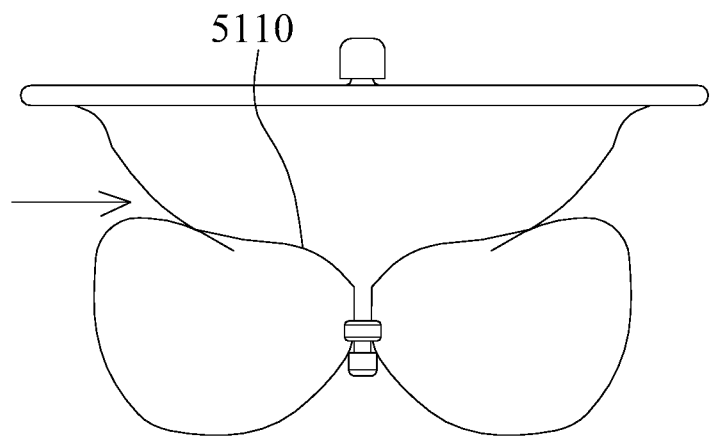
Figure 28:
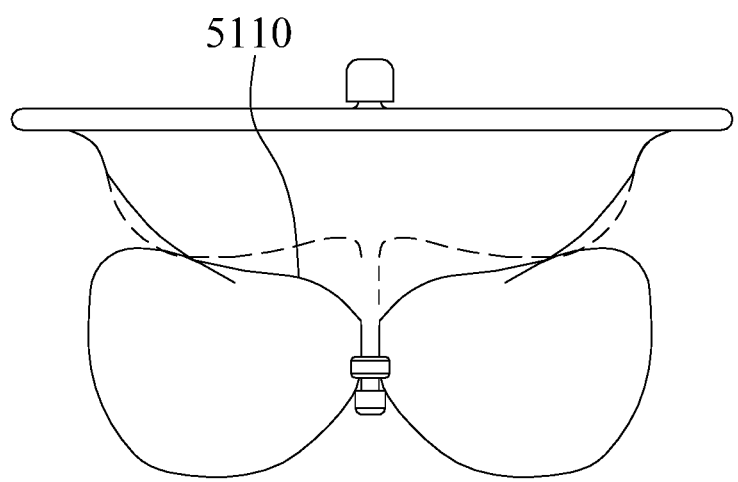
Figure 29:
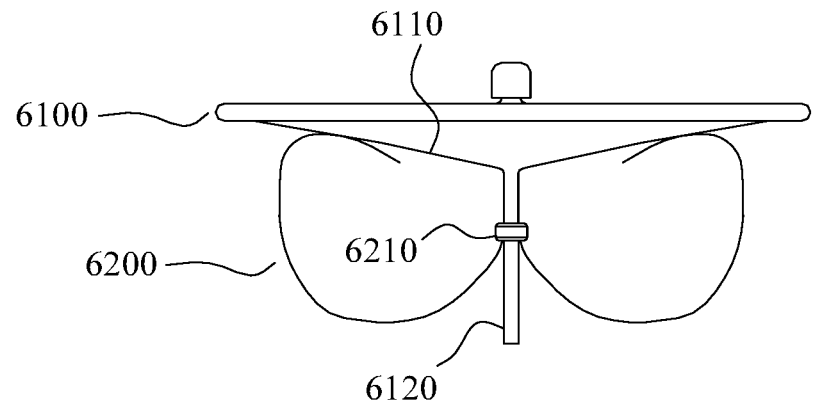
Figure 30:
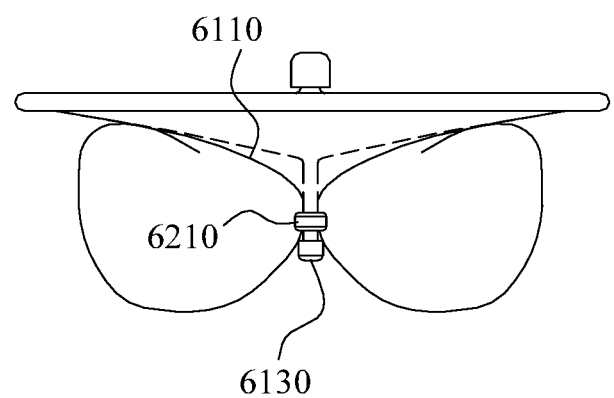

FIG. is an enlarged view illustrating a part indicated by circle A in FIG. 12A;

FIG. 13 is a schematic view illustrating a process of connecting an anchoring portion and a sealing portion according to the third embodiment;

FIG. 14 is a schematic view illustrating a left atrial appendage occluder according to a fourth embodiment;

FIGS. 15-17 are schematic views illustrating a process of releasing an anchoring portion according to a fifth embodiment, and the sealing portion is in a released state;

FIGS. 18-20 are schematic views illustrating sealing portions with disc bottoms in various shapes according to the fifth embodiment;

FIGS. 21-25 are schematic views comparing the disc bottom before and after deformation according to the fifth embodiment;

FIGS. 26-28 are schematic views comparing the disc bottom in another shape before and after deformation according to the fifth embodiment;

FIGS. 29-30 are schematic views comparing a disc bottom before and after deformation according to a sixth embodiment;

FIGS. 31-40 are schematic views illustrating a left atrial appendage occluder before and after assembly in various connection manners according to a seventh embodiment.

DETAILED DESCRIPTION OF ILLUSTRATED EMBODIMENTS

First Embodiment

Figure 1:
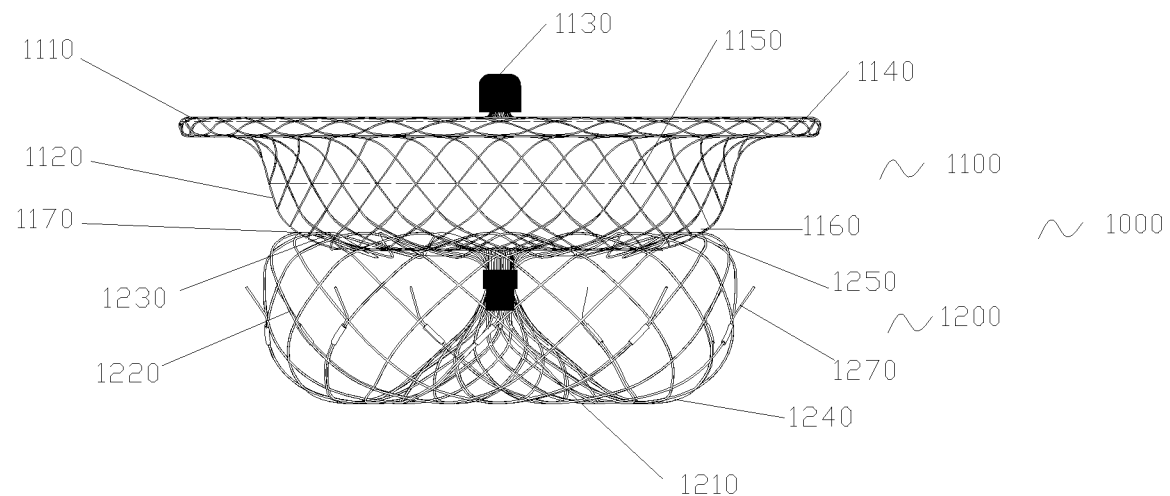
FIG. 1 is a schematic view illustrating a left atrial appendage occluder according to a first embodiment.

As illustrated in FIG. 1, the left atrial appendage occluder 1000 in the first embodiment of the present disclosure includes a sealing portion 1100 and an anchoring portion 1200 coupled to the sealing portion 1100. The sealing portion 1100 and the anchoring portion 1200 each are formed by weaving nickel-titanium wires.

The sealing portion 1100 includes a disc surface 1110, an intermediate part 1120, and a disc bottom 1170. An end of the disc surface 1110 is provided with a holding head 1130. One layer of PET flow blocking membrane 1140 is sutured inside the disc surface, one layer of flow blocking membrane 1150 is sutured inside a middle part of the intermediate part 1120, and one layer of flow blocking membrane 1160 is sutured inside the disc bottom 1170.

The anchoring portion 1200 includes an inner mesh-shaped cone 1210, an outer mesh-shaped cylinder 1220, an outer end bent portion 1230, an arc transition portion 1240 connected between the inner mesh-shaped cone 1210 and the outer mesh-shaped cylinder 1220, and an arc transition portion 1250 connected between the outer mesh-shaped cylinder 1220 and the outer end bent portion 1230. Multiple barbs 1270 are arranged uniformly circumferentially an outer surface of the outer mesh-shaped cylinder 1220.

The inner mesh-shaped cone 1210 forms an extending portion, the outer mesh-shaped cylinder 1220 forms a turning-back portion, and the outer end bent portion 1230 forms a necked opening portion.

A distal end of the disc bottom 1170 of the sealing portion 1100 (that is, an end of the disc bottom 1170 closer to the anchoring portion 1200) is connected with a proximal end of the inner mesh-shaped cone 1210 of the anchoring portion 1200 (that is, an end of the inner mesh-shaped cone 1210 closer to the sealing portion 1100) in a rigid-sleeve fastening manner or a laser welding manner.

Figure 2:
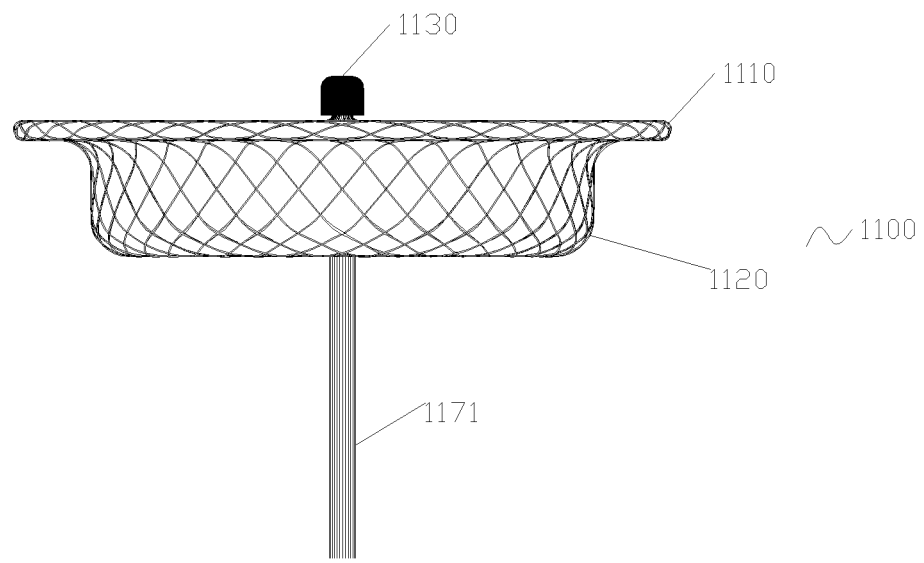
FIG. 2 is a schematic view illustrating a sealing portion after thermoforming according to the first embodiment.
Figure 3:
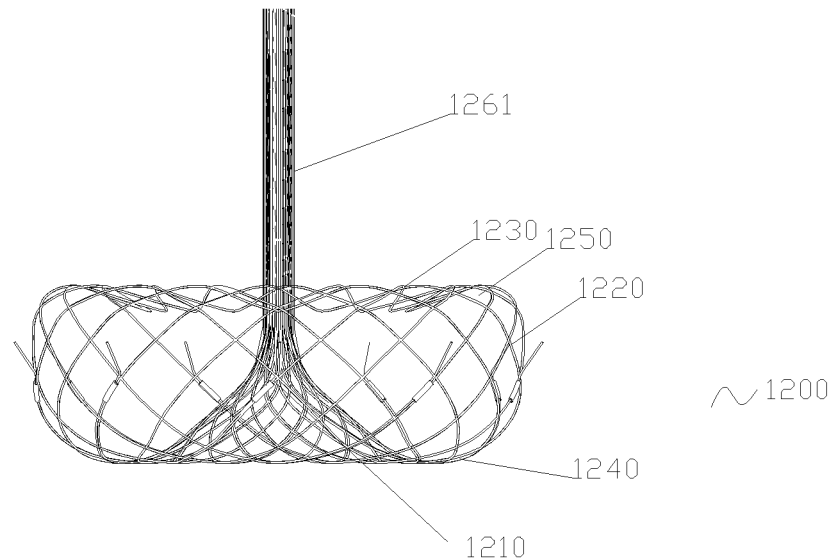
FIG. 3 is a schematic view illustrating an anchoring portion after thermoforming according to the first embodiment.

Before being connected with each other, the sealing portion 1100 and the anchoring portion 1200 are individually shaped by a cylindrical woven nickel-titanium mesh through high-temperature heat treatment within a mold. FIG. 2 illustrates the sealing portion 1100 of the left atrial appendage occluder 1000 shaped through thermoforming according to the first embodiment of the present disclosure. FIG. 3 illustrates the anchoring portion 1200 of the left atrial appendage occluder 1000 shaped through thermoforming according to the first embodiment of the present disclosure. The sealing portion 1100 is provided with a distal nickel-titanium wire which is constricted and converged, and the anchoring portion 1200 is provided with a proximal nickel-titanium wire which is constricted and converged.

FIGS. 4A-7 illustrate a connection manner of the sealing portion 1100 and the anchoring portion 1200 of the left atrial appendage occluder 1000 according to the first embodiment of the present disclosure.

Figure 4A:
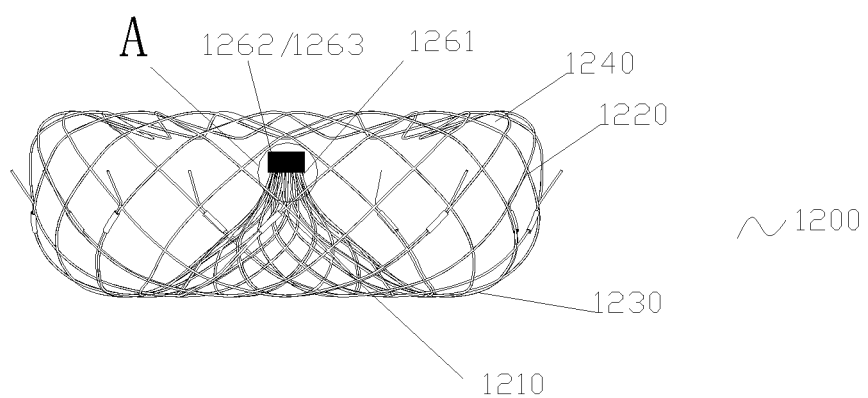
FIG. 4A is a schematic view illustrating a process of connecting the anchoring portion and the sealing portion (only the anchoring portion is illustrated) according to the first embodiment.
Figure 4B:
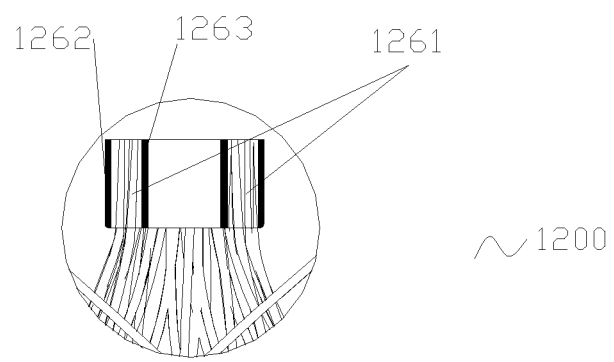
FIG. 4B is an enlarged view illustrating a part indicated by circle A in FIG. 4A.

The proximal nickel-titanium wire 1261 of the anchoring portion 1200 is converged and fixed between an outer steel sleeve 1262 (equivalent to an outer ring) and an inner steel sleeve 1263 (equivalent to an inner ring). It can be seen that the nickel-titanium wire used for weaving the anchoring portion 1200 is constricted and converged at a proximal end of the extending portion and is connected between the inner steel sleeve 1263 and the outer steel sleeve 1262 serving as a connector. As can be seen in FIG. 4A, the inner steel sleeve 1263 and the outer steel sleeve 1262 serving as the connector are disposed farther away from the sealing portion 1100 than the necked opening portion. The anchoring portion 1200 in a turning-up structure is substantially in a shape of a bowl (or nest), and the connector is disposed within the bowl and below an opening of the bowl.

The inner steel sleeve 1263, the outer steel sleeve 1262, and the proximal nickel-titanium wire 1261 extending between the inner steel sleeve 1263 and the outer steel sleeve 1262 are fixed together by welding or in a pressing manner. The inner steel sleeve 1263 is in a hollow structure, and an excess portion of the proximal nickel-titanium wire 1261 extending beyond a proximal end of the outer steel sleeve 1262 is removed by shearing or laser processing.

Figure 5:
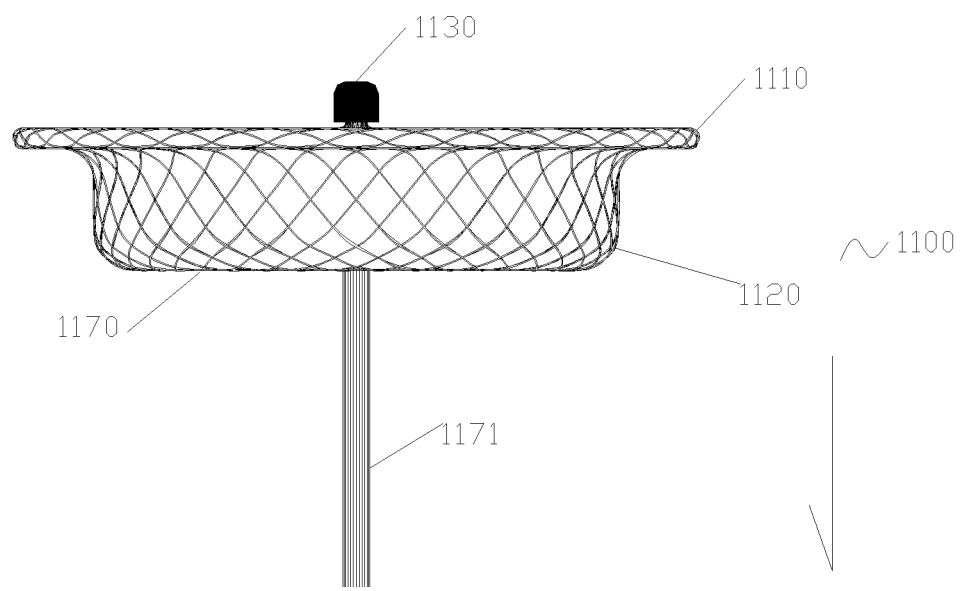
FIG. 5 is a schematic view illustrating the process of connecting the anchoring portion and the sealing portion (only the sealing portion is illustrated) according to the first embodiment.
Figure 6:
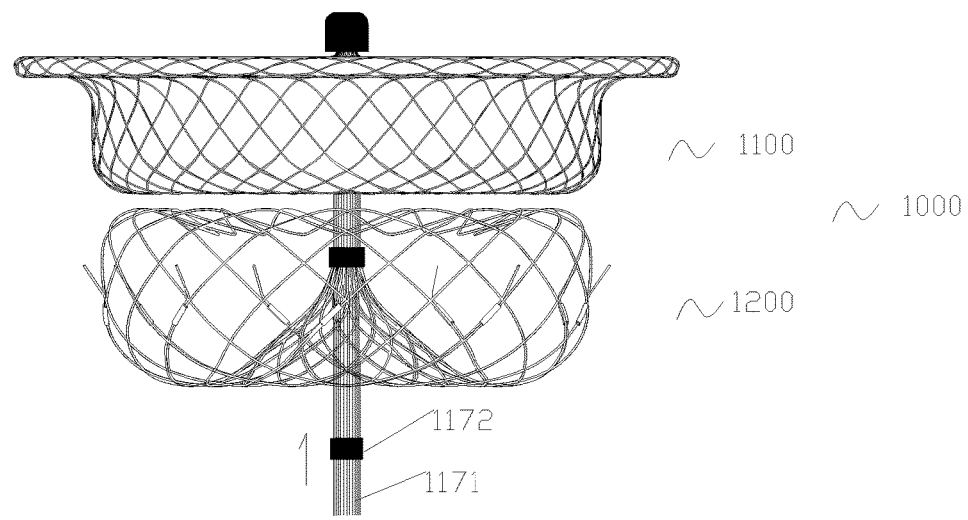
FIG. 6 is a schematic view illustrating that the anchoring portion and the sealing portion start to connect according to the first embodiment.

As illustrated in FIG. 5 and FIG. 6, the distal nickel-titanium wire 1171 of the sealing portion 1100 is converged at a middle part of the disc bottom 1170 and extends through the inner steel sleeve 1263. A certain pulling force can be applied to tightly connect the sealing portion 1100 and the anchoring portion 1200 to generate a certain pre-tightening force. The pre-tightening force enables the intermediate part 1120 of the sealing portion 1100 to form a tapered structure, and meanwhile an overall height of the left atrial appendage occluder 1000 can be reduced.

Figure 7A:
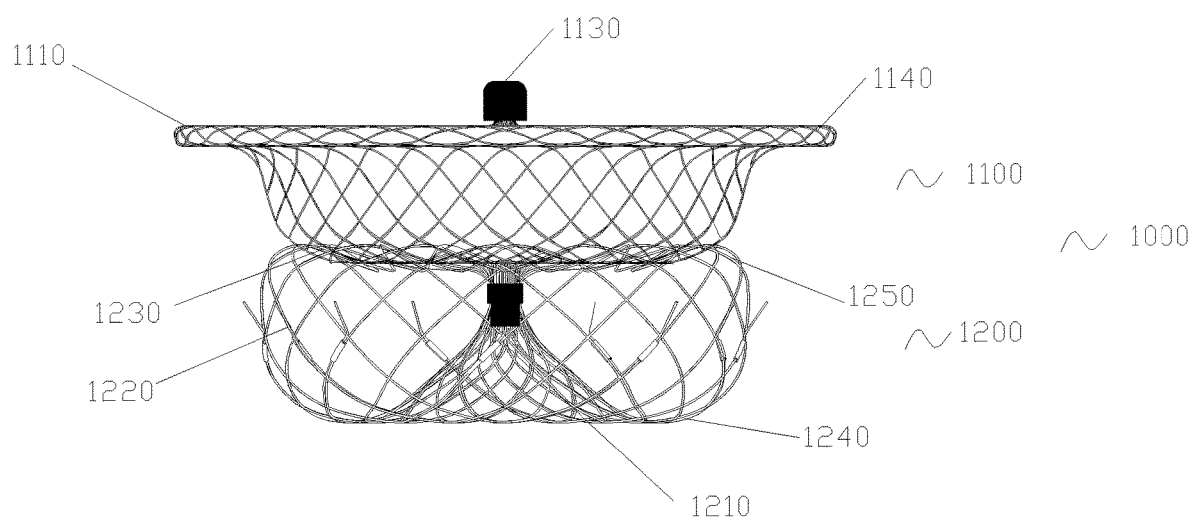
FIG. 7A is a schematic view illustrating that a connection between the anchoring portion and the sealing portion is completed according to the first embodiment.
Figure 7B:
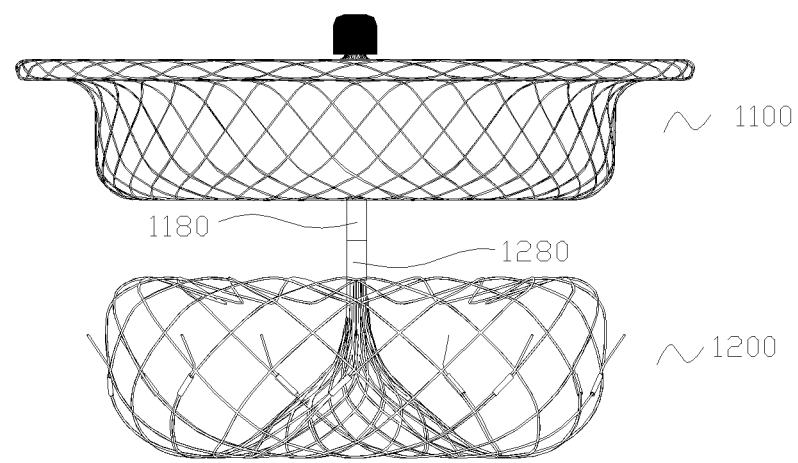
FIG. 7B is a schematic view illustrating a connection between a sealing portion and an anchoring portion in the related art.
Figure 7C:
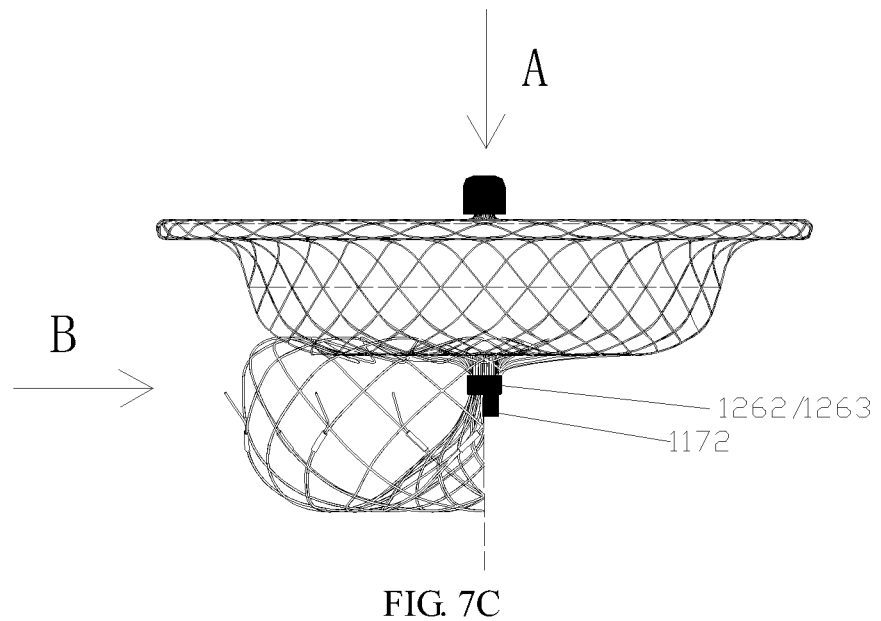
FIG. 7C is a schematic view illustrating the anchoring portion and the sealing portion illustrated in FIG. 7A with a part omitted.

FIGS. 7A-7C illustrate a structure of the sealing portion 1100. The distal nickel-titanium wire 1171 of the sealing portion 1100 is fixed with a steel sleeve 1172 (equivalent to a retainer). The steel sleeve 1172 can be slidably moved along the distal nickel-titanium wire 1171 to abut against a distal end of the inner steel sleeve 1263 and be further fixed to the distal nickel-titanium wire 1171. An outer diameter of the steel sleeve 1172 is larger than an inner diameter of the inner steel sleeve 1263 to prevent the distal nickel-titanium wire 1171 from disengaging off from the inner steel sleeve 1263.

An excess portion of the distal nickel-titanium wire 1171 extending beyond a distal end of the sealing portion 1100 is removed by shearing or laser processing. A material of the steel sleeve according to the present disclosure may be stainless steel, nickel-titanium alloy, or other metal material that meets biocompatibility requirements. In this embodiment, the material of the steel sleeve is stainless steel.

During assembling, the sealing portion 1100 and the anchoring portion 1200 are moved toward each other. When the sealing portion 1100 and the anchoring portion 1200 are just in contact with each other, the sealing portion 1100 and the anchoring portion 1200 is in a first state. As the distal nickel-titanium wire 1171 is further pulled axially, a side of the sealing portion 1100 facing the anchoring portion 1200 increasingly tightly abuts against the anchoring portion 1200 to generate a stress (i.e., the pre-tightening force). When the distal nickel-titanium wire 1171 is pulled axially a predetermined distance, the sealing portion 1100 and the anchoring portion 1200 is in a second state, and at this time, the sealing portion 1100 and the anchoring portion 1200 are further kept in the second state via the steel sleeve 1172, such that the stress is maintained.

The predetermined distance that the distal nickel-titanium wire 1171 is pulled axially may be directly obtained by measurements, or may be obtained according to changes in a shape of the side of the sealing portion 1100 facing the anchoring portion 1200 (i.e., the disc bottom 1170), or may be obtained by directly measuring a tensile force of the distal nickel-titanium wire 1171 or a stress between the sealing portion 1100 and the anchoring portion 1200.

The changes in the shape of the disc bottom 1170 can be determined by comparing with the shape of the disc bottom 1170 itself in the first state, and can also be determined by comparing with an angle between the disc bottom 1170 and the intermediate part 1120 or an angle between the disc bottom 1170 and an axial of the sealing portion 1100.

Compared with the sealing portion 1100 and the anchoring portion 1200 illustrated in FIG. 6, the sealing portion 1100 and the anchoring portion 1200 in the first state are further brought into just contact with each other. Since the shape of the sealing portion 1100 are unchanged, the shape of the sealing portion 1100 in the first state can refer to that illustrated in FIG. 6. As illustrated in FIG. 6 and FIG. 7A, it can be clearly seen that in the first state, the disc bottom 1170 is substantially perpendicular to the intermediate part 1120, and in the second state as illustrated in FIG. 7A, the angle between the disc bottom 1170 and the intermediate part 1120 is increased, and the middle part of the disc bottom 1170 in a radial direction further protrudes toward the anchoring portion 1200. Therefore, the predetermined distance that the distal nickel-titanium wire 1171 is pulled axially can be indicated and controlled with respect to changes in the angle.

After the sealing portion 1100 is connected to the anchoring portion 1200, one layer of PET flow blocking membrane 1140 is sutured inside the disc surface of the sealing portion 1100 of the left atrial appendage occluder 1000, one layer of flow blocking membrane 1150 is sutured inside the middle part of the intermediate part 1120 of the sealing portion 1100, and one layer of flow blocking membrane 1160 is sutured inside the disc bottom 1170 of the sealing portion 1100, as illustrated in FIG. 1.

The sealing portion 1100 is a cage-shaped structure having a certain internal space as a whole, and in a presetting state, the intermediate part is in a substantially cylindrical shape. It can be seen by comparing FIG. 2 with FIG. 7A, after assembly, the disc bottom 1170 and the necked opening portion are tightly abutted against each other, and a distal end of the intermediate part is radially constricted to have a certain taper and forms a substantially inverted-cone-shaped structure. Moreover, the middle part of the disc bottom 1170 protrudes toward the anchoring portion 1200 under the action of the pre-tightening force.

Referring to FIG. 7B, in the related art, the sealing portion 1100 is provided with a connection part 1180, and the anchoring portion 1200 is provided with a connection part 1280. The connection part 1180 of the sealing portion 1100 and the connection part 1280 of the anchoring portion 1200 are arranged in align with and extend toward each other. When the connection part 1180 and the connection part 1280 come in contact with each other, the connection part 1180 and the connection part 1280 are fixedly connected together by welding or via an annular hoop.

It can be seen that, since a larger gap exists between the sealing portion 1100 and the anchoring portion 1200, the sealing effect needs to be improved.

In this embodiment, the sealing portion 1100 and the anchoring portion 1200 have respective converging parts operating as the connection parts. As illustrated in FIG. 5, the connection part of the sealing portion 1100 (i.e., the converged distal nickel-titanium wire 1171) is formed by converging the disc bottom 1170, that is, the disc bottom 1170 with a larger cross-section area converges abruptly to form one wire strand with a smaller cross-section area.

Combining with the FIG. 4A, it can be seen that, the connection part 1280 of the anchoring portion 1200, namely, the proximal nickel-titanium wire 1261 which has been converged, gradually transforms into a strand with a smaller cross-section area from the inner mesh-shaped cone 1210.

Referring to FIG. 7C, after assembly, the connection part of the anchoring portion 1200 is fixed between the outer steel sleeve 1262 and the inner steel sleeve 1263, and the connection part of the sealing portion 1100 extends through the inner steel sleeve 1263 and is fixed with the steel sleeve 1172 abutted against the distal end of the inner steel sleeve 1263. In this connection manner, the connection part of the sealing portion 1100 extends through a center void space inside the connection part of the anchoring portion 1200, and the connection part of the anchoring portion 1200 is disposed around the connection part of the sealing portion 1100, such that two connection parts are arranged with one connection part nested within the other connection part, and each of two connection parts extends beyond a terminal end of the other connection part.

As seen from a direction of an axial of the left atrial appendage occluder (i.e., direction A illustrated in FIG. 7C), the connection part of the sealing portion 1100 is nested within the connection part of the anchoring portion 1200. The connection part of the sealing portion 1100 and the connection part of the anchoring portion 1200 individually extend along a straight line (that is, extend along the direction of the axial of the left atrial appendage occlude). Due to the staggered arrangement, the connection part of the anchoring portion 1200 and the connection part of the sealing portion 1100 extend without spatially interference with each other, such that an axial distance between the sealing portion 1100 and the anchoring portion 1200 can be decreased as much as possible until peripheral regions each around the connection parts of the anchoring portion 1200 and the sealing portion 1100, respectively, are tightly abutted against one another.

As seen from a direction perpendicular to the axial of the left atrial appendage occluder (i.e., direction B illustrated in FIG. 7C), the connection part of the anchoring portion 1200 and the connection part of the sealing portion 1100 overlap each other, and a projection of the connection part of the sealing portion 1100 in direction B falls within the connection part of the anchoring portion 1200.

In this embodiment, the sealing portion 1100 is integrated with the connection part of the sealing portion 1100, and the anchoring portion 1200 is integrated with the connection part of the anchoring portion 1200. Alternatively, it is also possible that the sealing portion 1100 and the anchoring portion 1200 are formed without wire strands extending toward each other and provided with their respective connection rods instead. That is, the sealing portion 1100 and the anchoring portion 1200 are provided individually with their respective connection rods. The connection rods each are disposed at middle parts of opposite sides of the sealing portion 1100 and the anchoring portion 1200 respectively, and one of the connection rods is in a shape of a hollow structure, and the other connection rod extends through the one connection rod, such that a connection between the sealing portion 1100 and the anchoring portion 1200 in the staggered manner can also be realized.

Figure 8:
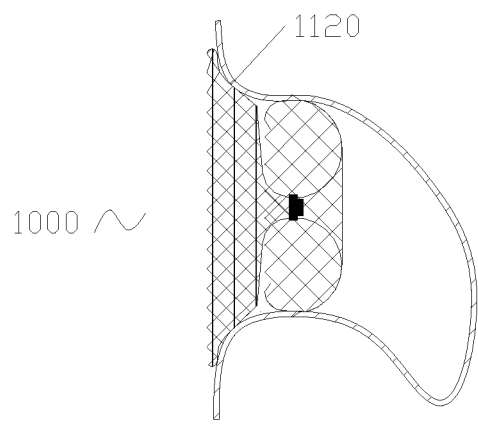
FIG. 8 is a schematic view illustrating a left atrial appendage occluder released in a left atrial appendage according to the first embodiment.

As illustrated in FIG. 8, when the left atrial appendage occluder 1000 in this embodiment is delivered into the left atrial appendage via a percutaneous catheter delivery system, the left atrial appendage occluder 1000 is anchored in the left atrial appendage. The anchoring portion 1200 is connected to the sealing portion 1100 such that the pre-tightening force is formed between the sealing portion 1100 and the anchoring portion 1200, and the intermediate part 1120 in a tapered shape of the left atrial appendage occluder 1000 can be more closely attached to an orifice of the left atrial appendage. The pre-tightening force allows the disc surface 1110 of the sealing portion 1100 to be attached to the left atrial appendage more closely, such that the three-layered membrane effectively blocks blood from flowing into the left atrial appendage to reduce the incidence of endoleaks.

Second Embodiment

Figure 9A:
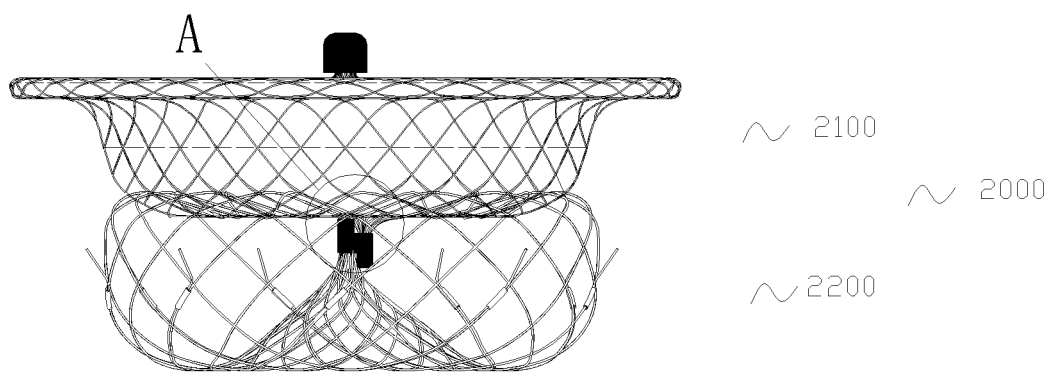
FIG. 9A is a schematic view illustrating a left atrial appendage occluder according to a second embodiment.
Figure 9B:
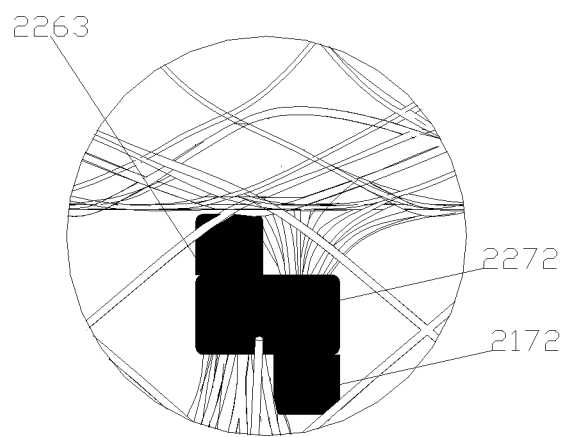
FIG. 9B is an enlarged view illustrating a part indicated by circle A in FIG. 9A.

In the second embodiment according to the present disclosure, the left atrial appendage occluder 2000 includes a sealing portion 2100 and an anchoring portion 2200. After thermoforming, a shape of the sealing portion 2100 and a shape of the anchoring portion 2200 are the same as that in the first embodiment respectively. Compared with the first embodiment, a connection manner between the sealing portion 2100 and the anchoring portion 2200 is different, as illustrated in FIG. 9A and FIG. 9B.

In the second embodiment of the present disclosure, the left atrial appendage occluder 2000 includes the sealing portion 2100 and the anchoring portion 2200 after thermoforming. The sealing portion 2100 is provided with a distal nickel-titanium wire which is constricted and converged, and the anchoring portion 2200 is provided with a proximal nickel-titanium wire which is constricted and converged.

Figure 10:
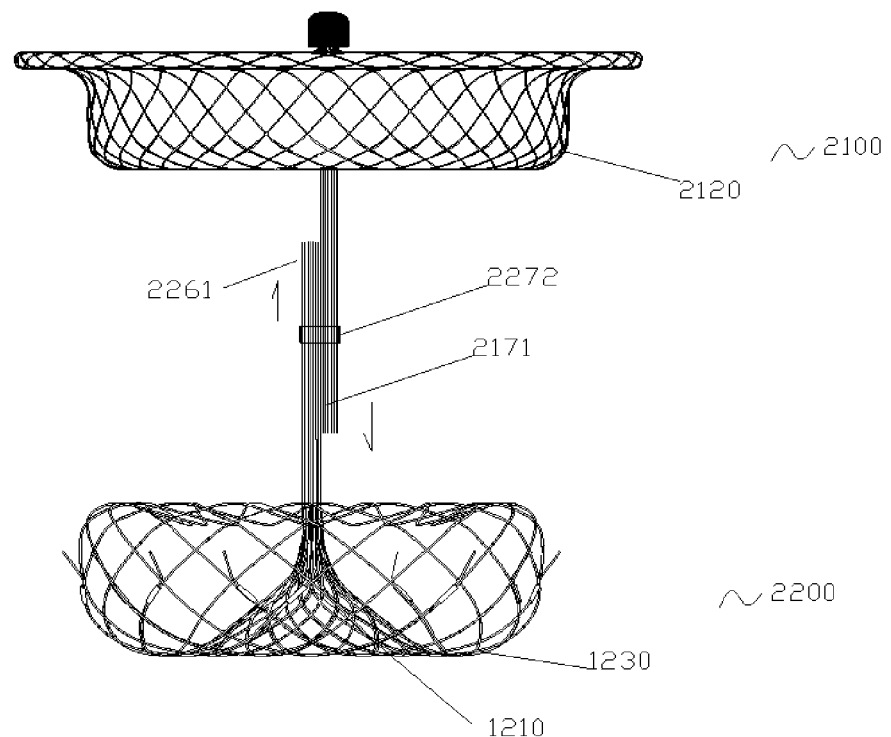
FIG. 10 is a schematic view illustrating a process of connecting an anchoring portion and a sealing portion according to the second embodiment.

As illustrated in FIG. 10, a distal nickel-titanium wire 2171 of the sealing portion 2100 and a proximal nickel-titanium wire 2261 of the anchoring portion 2200 in this embodiment are individually processed to be constricted and converged, and then extend through a steel sleeve 2272 (equivalent to a body of a connector) from opposite directions respectively.

Two pulling forces are applied to the distal nickel-titanium wire 2171 and the proximal nickel-titanium wire 2261 along directions indicated by arrows illustrated in FIG. 10 correspondingly, such that the sealing portion 2100 and the anchoring portion 2200 are tightly connected with each other to generate a certain pre-tightening force between the sealing portion 2100 and the anchoring portion 2200, and the pre-tightening force allows the intermediate part 2120 of the sealing portion 2100 to be stretched into a shape of a tapered structure. Furthermore, as illustrated in FIG. 9B, the proximal nickel-titanium wire 2261 of the anchoring portion 2200 extends through a steel sleeve 2172 and is fixed with the steel sleeve 2172 by welding or in a pressing manner, and the distal nickel-titanium wire 2171 of the sealing portion 2100 extends through a steel sleeve 2263 and is fixed with the steel sleeve 2263 by welding or in a pressing manner. The steel sleeve 2172 and the steel sleeve 2263 are engaged on either sides of a steel sleeve 2272, and an excess portion of the proximal nickel-titanium wire 2261 extending beyond an distal end of the steel sleeve 2172 and an excess portion of the distal nickel-titanium wire 2171 extending beyond an proximal end of the steel sleeve 2263 are removed by shearing or laser processing.

As illustrated in FIG. 9B, the sealing portion 2100 and the anchoring portion 2200 in this embodiment are also provided in a similar manner to the first embodiment, and each have and are integrated with their connection parts extending toward each other, respectively. Compared with the sealing portion 1100 and the anchoring portion 1200 in the first embodiment, the two connection parts of the sealing portion 2100 and the anchoring portion 2200 are staggered from each other in a mutually offset manner. According to the orientations illustrated in FIG. 9B, one of the two connection parts is to the left and the other is to the right.

In this way, it is also possible to avoid spatial interference between the two connection parts when extending toward each other, such that the sealing portion 2100 and the anchoring portion 2200 can be brought to each other as close as possible.

Third Embodiment

Figure 11A:
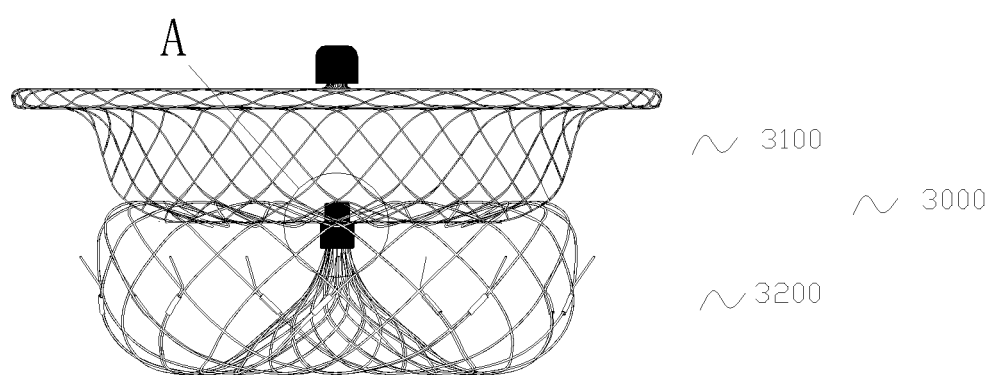
FIG. 11A is a schematic view illustrating a left atrial appendage occluder according to a third embodiment.
Figure 11B:
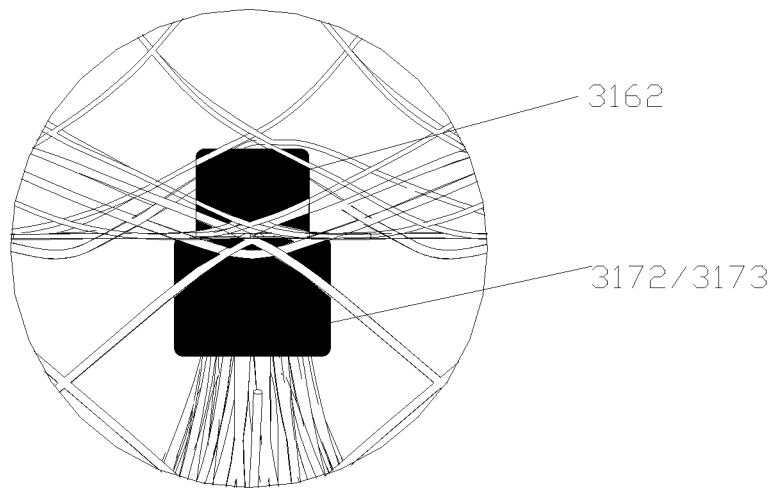
FIG. 11B is an enlarged view illustrating a part indicated by circle A in FIG. 11A.

In the third embodiment according to the present disclosure, the left atrial appendage occluder 3000 includes a sealing portion 3100 and an anchoring portion 3200. After thermoforming, a shape of the sealing portion 3100 and a shape of the anchoring portion 3200 are the same as that in the first embodiment, as well as the second embodiment, respectively. Compared with the first embodiment as well as the second embodiment, a connection manner between the sealing portion 3100 and the anchoring portion 3200 is different, as illustrated in FIG. 11A and FIG. 11B.

Figure 12B:
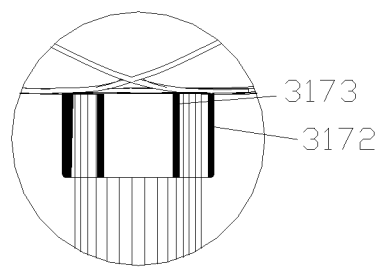

In the third embodiment of the present disclosure, the left atrial appendage occluder 3000 includes the sealing portion 3100 and the anchoring portion 3200 after thermoforming. The sealing portion 3100 is provided with a distal nickel-titanium wire which is constricted and converged, and the anchoring portion 3200 is provided with a proximal nickel-titanium wire which is constricted and converged. FIGS. 12A-13 illustrate another connection manner between the sealing portion 3100 and the anchoring portion 3200 of the left atrial appendage occluder 3000 according to the third embodiment of the present disclosure.

In the left atrial appendage occluder 3000 of this embodiment, a distal nickel-titanium wire 3171 of the anchoring portion 3100 is converged and extends between an outer steel sleeve 3172 and an inner steel sleeve 3173, and the outer steel sleeve 3172 and the inner steel sleeve 3173, and the distal nickel-titanium wire 3171 extending between the outer steel sleeve 3172 and the inner steel sleeve 3173 are fixed together by welding or in a pressing manner. The inner steel sleeve 3173 is in a shape of a hollow structure, and an excess portion of the distal nickel-titanium wire 3171 extending beyond distal ends of the outer steel sleeve 3172 and the inner steel sleeve 3173 is removed by shearing or laser processing.

The proximal nickel-titanium wire 3261 of the anchoring portion 3200 is converged and extends through the inner steel sleeve 3173 disposed at a distal end of the sealing portion 3200 to extend into a middle part of the sealing portion 3100. A certain pulling force can be applied to tightly connect the sealing portion 3100 with the anchoring portion 3200 to generate a certain pre-tightening force, and the pre-tightening force enables an intermediate part of the sealing portion 3100 to be reshaped in a tapered structure. Further, the proximal nickel-titanium wire 3261 of the anchoring portion 3200 is fixed together with a steel sleeve 3162. An outer diameter of the steel sleeve 3162 is larger than an inner diameter of the inner steel sleeve 3173, and an excess portion of the proximal nickel-titanium wire 3261 extending beyond a proximal end of the anchoring portion 3200 is removed by shearing or laser processing.

Fourth Embodiment

Compared with the first embodiment, the shape of a sealing portion 4100 in the fourth embodiment is different, as illustrated in FIG. 14.

In this embodiment, the sealing portion 4100 is in a substantially flat disk shape, that is, the sealing portion 4100 is a sealing disk. Under the action of a pre-tightening force, a middle part of the sealing disk protrudes toward the anchoring portion.

Fifth Embodiment

This embodiment mainly illustrates a release of an anchoring portion 5200 and changes in the shape of a sealing portion 5100 during assembly. Specific structures of the anchoring portion 5200 and the sealing portion 5100 can refer to at least one of the first embodiment, the second embodiment, and the third embodiment.

As illustrated in FIGS. 15-17, the left atrial appendage occluder in this embodiment includes the sealing portion 5100 and the anchoring portion 5200 coupled to the sealing portion 5100. The anchoring portion 5200 is compressed and received within a sheath tube before being released, thereby facilitating the left atrial appendage occluder to be delivered to a lesion in a body. In a compressed state, the anchoring portion 5200 is in a cylindrical structure, and portion A is positioned on an inner wall of the cylindrical structure. When the anchoring portion 5200 is released in a turning-up manner (a direction of turning-up can refer to a direction indicated by an arrow illustrated in FIG. 16), portion A on the inner wall of the cylindrical structure is gradually bent outward, and finally abuts against a disc bottom of the sealing portion 5100.

As illustrated in FIGS. 18-20, the sealing portion 5100 includes a disc surface, an intermediate part, and a disc bottom 5110. A central part of the disc bottom 5110 (that is, a part of the disc bottom 5110 disposed in a center of the disc bottom 5110) is constricted and converged to form a distal nickel-titanium wire 5120, and the distal nickel-titanium wire 5120 extends through a connector 5210 of the anchoring portion 5200 (such as, a steel sleeve, or the like).

The shape of a middle part of the disc bottom 5110 (that is, a part of the disc bottom 5110 disposed in a middle of the disc bottom 5110) varies in various examples. As illustrated in FIG. 18, the middle part of the disc bottom 5110 may be recessed away from the anchoring portion 5200. As illustrated in FIG. 19, the middle part of the disc bottom 5110 may be in a substantially flat shape. As illustrated in FIG. 20, the middle part of the disc bottom 5110 may be protruded toward the anchoring portion 5200.

The above examples illustrate characteristics of the shape of the disc bottom 5110 before completing the assembly of the left atrial appendage occluder (i.e., a pre-tightening force is not applied). When the pre-tightening force is applied, the middle part of the disc bottom 5110 has different degrees of deformation and is generally further moved toward the anchoring portion 5200.

Referring to FIGS. 21-25, taking the disc bottom 5110 in one shape as an example, the sealing portion 5100 and the anchoring portion 5200 are assembled together after being individually processed and thermoformed. The distal nickel-titanium wire 5120 first extends through the connector 5210 of the anchoring portion 5200 to enable the sealing portion 5100 and the anchoring portion 5200 to move axially toward each other.

Figure 22:
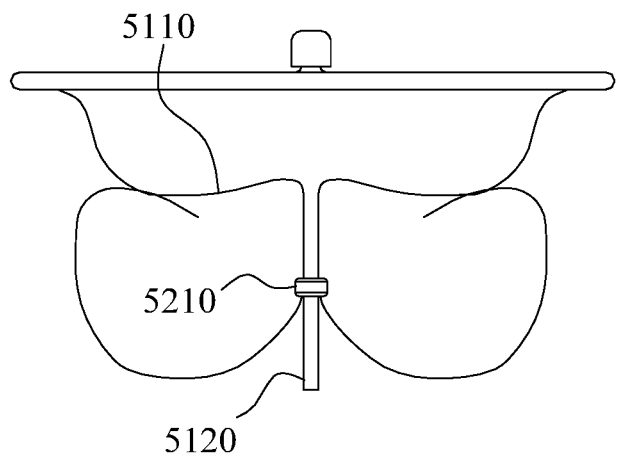
Figure 23:
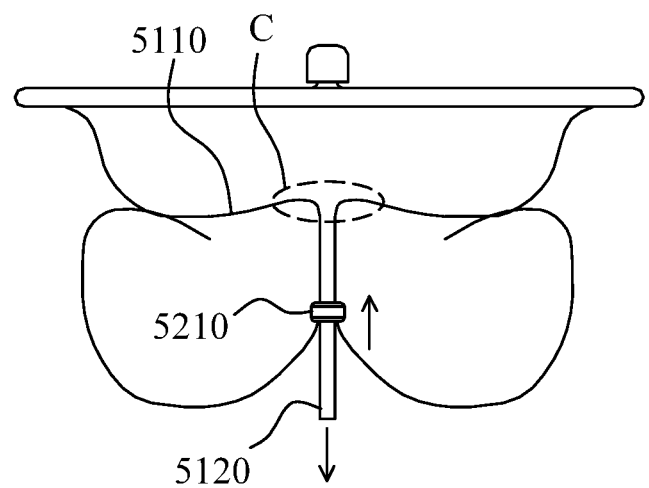
Figure 24:
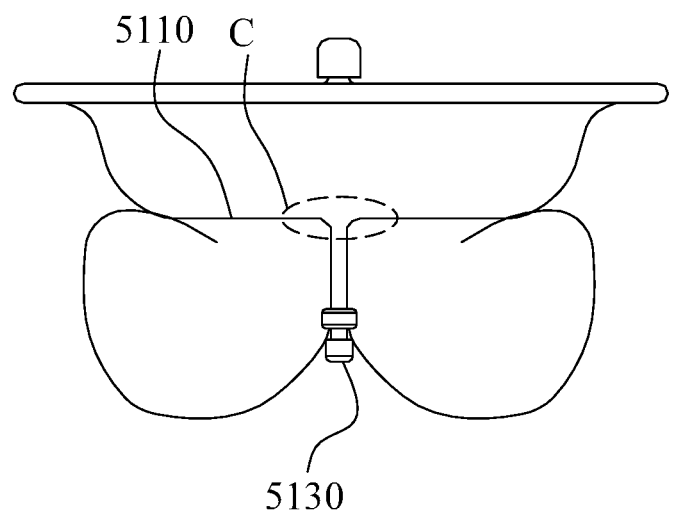
Figure 25:
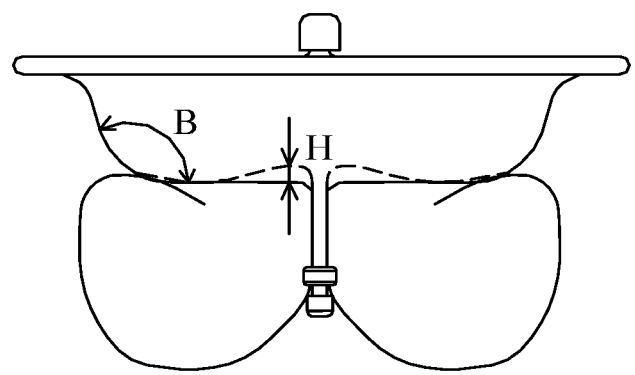

As illustrated in FIG. 22, the sealing portion 5100 and the anchoring portion 5200 are in a first state. In the first state, the sealing portion 5100 and the anchoring portion 5200 are just in contact with each other and the pre-tightening force is not applied, and middle region C of the disc bottom 5110 has a tendency to recess away from the anchoring portion 5200. The distal nickel-titanium wire 5120 is then pulled downward in a direction of a downward-arrow illustrated in FIG. 23, and the connector 5210 of the anchoring portion 5200 moves upward in a direction of an upward-arrow, such that middle region C is deformed to generate a predetermined deformation or to meet requirements of a pre-tightening force. Furthermore, the distal nickel-titanium wire 5120 is fixed with a retainer 5130, at this time, the sealing portion 5100 and the anchoring portion 5200 are in a second state. As illustrated in FIG. 24, the middle region C is deformed into a substantially flat shape.

A change of angle B or an axial deformation H of middle region C can be acquired when the pre-tightening force is applied, so as to control an assembling process. A deformation of middle region C is more clearly illustrated by a comparison indicated in FIG. 25, and a dotted line indicates a position of middle region C in the first state.

Referring to FIGS. 26-28, in another implementation, the sealing portion 5100 and the anchoring portion 5200 are in the first state. In the first state, the sealing portion 5100 and the anchoring portion 5200 are just in contact with each other and the pre-tightening force is not applied, and middle region C of the disc bottom 5110 has a tendency to recess away from the anchoring portion 5200. During assembling, the distal nickel-titanium wire 5120 is pulled downward and the connector 5210 of the anchoring portion 5200 moves upward until middle region C is deformed to generate a predetermined deformation or to meet requirements of a pre-tightening force. Furthermore, the distal nickel-titanium wire 5120 is fixed with a retainer 5130, and at this time, the sealing portion 5100 and the anchoring portion 5200 are in the second state. When middle region C is forced to deform, the intermediate part of the sealing portion 5100 is converged radially along a direction of an arrow illustrated in FIG. 27. In the second state, as more clearly illustrated by a comparison indicated in FIG. 28, the intermediate part together with the disc bottom 5110 are in an inverted-cone-shape as a whole, and a dotted line in FIG. 28 indicates a position of the intermediate part and middle region C in the first state.

Sixth Embodiment

Referring to FIG. 29 and FIG. 30, the left atrial appendage occluder in this embodiment includes a sealing portion 6100 and an anchoring portion 6200. In the first state, a side of the sealing portion 6100 facing the anchoring portion 6200 is provided with a disc bottom 6110 in an inverted-cone-shaped. A central part of the disc bottom 6110 (that is, a part of the disc bottom 6110 disposed in a center of the disc bottom 6110) is constricted and converged to form a distal nickel-titanium wire 6120, and the distal nickel-titanium wire 6120 extends through a connector 6210 of the anchoring portion 6200 (such as, a steel sleeve, or the like).

In the second state after assembly, a middle part of the disc bottom 6110 (that is, a part of the disc bottom 6110 disposed in a middle of the disc bottom 6110) is further brought closer to the connector 6210, a taper of the middle part of the disc bottom 6110 is increased, and the distal nickel-titanium wire 6120 is locked in an axial position via a retainer 6130.

Seventh Embodiment

This embodiment mainly illustrates a different connection manner between an anchoring portion 7200 and a sealing portion 7100. Specific structures of the anchoring portion 7200 and the sealing portion 7100 can refer to at least one of the other embodiments.

Referring to figures provided in this embodiment, the left atrial appendage occluder includes a sealing portion 7100 and an anchoring portion 7200 coupled with the sealing portion 7100. The sealing portion 7100 includes a disc surface, an intermediate part, and a disc bottom 7110.

Figure 31:
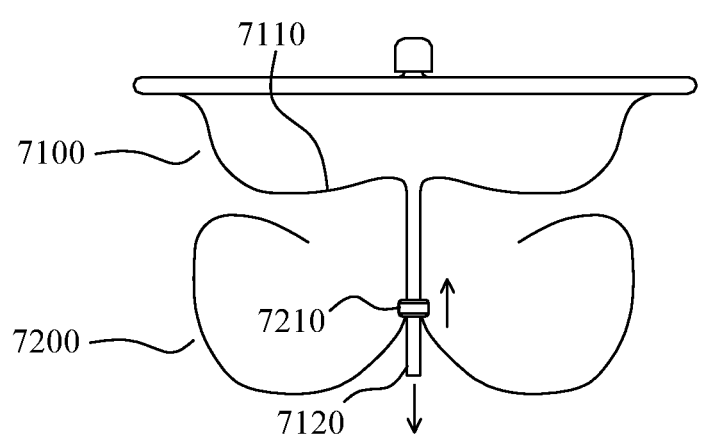
Figure 32:
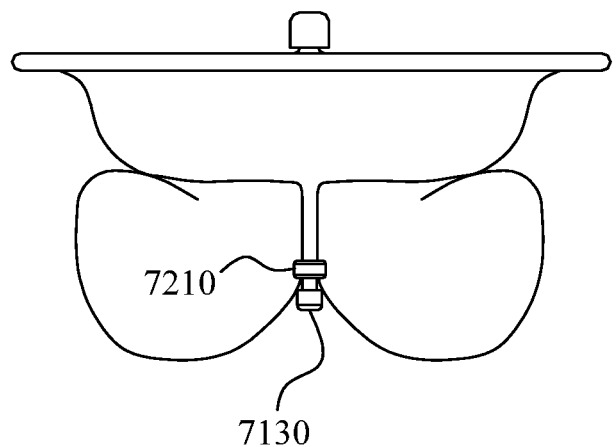

As illustrated in FIG. 31 and FIG. 32, a central part of a disc bottom 7110 is constricted and converged to form a connection part, that is, the central part of the disc bottom 7110 is converged to form a distal nickel-titanium wire 7120. A middle part of the anchoring portion 7200 is wholly converged to form a connection part, and an end of the connection part of the anchoring portion 7200 is fixed with a connector 7210 (for example, a steel sleeve). When assembling, the distal nickel-titanium wire 7120 extends through a hollow portion of the connector 7210 of the anchoring portion 7200 and is tensioned against the anchoring portion 7200 to generate a pre-tightening force. When the anchoring portion 7200 and the sealing portion 7100 abut tightly against each other, and a middle part of the disc bottom 7110 is deformed to further protrude toward the anchoring portion 7200. Finally, the distal nickel-titanium wire 7120 is fixed with the retainer 7130 (for example, a steel hoop), and an excess portion of the distal nickel-titanium wire 7120 beyond a distal end of the retainer 7130 is cut off to complete assembly.

Figure 33:
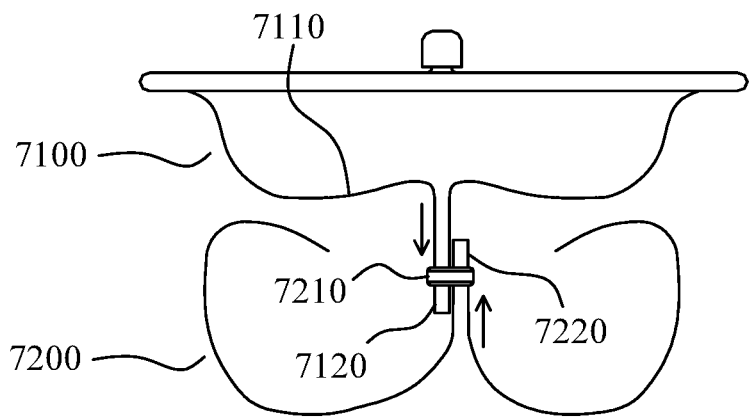
Figure 34:
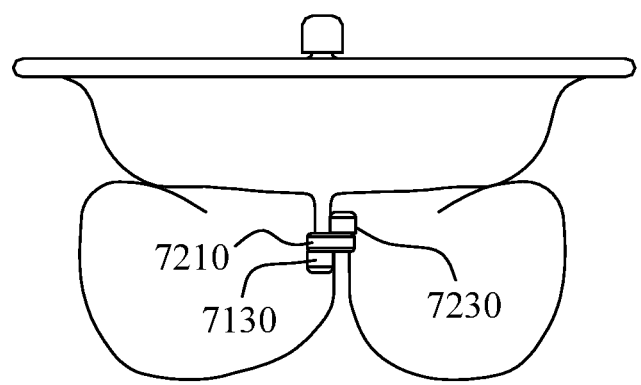

In another implementation, as illustrated in FIG. 33 and FIG. 34, the central part of the disc bottom 7110 is constricted and converged to form the connection part, that is, the central part of the disc bottom 7110 is converged to form the distal nickel-titanium wire 7120.

The middle part of the anchoring portion 7200 is wholly converged to form a proximal nickel-titanium wire 7220. A connector 7210 with two passages arranged side by side is provided, and the distal nickel-titanium wire 7120 and the proximal nickel-titanium wire 7220 extend through the two passages correspondingly in opposite directions and are oppositely tensioned to generate a pre-tightening force. When the anchoring portion 7200 and the sealing portion 7100 abut tightly against each other, and the middle part of the disc bottom 7110 is deformed to further protrude toward the anchoring portion 7200. Finally, the distal nickel-titanium wire 7120 is fixed with the retainer 7130 (for example, a steel hoop), and an excess portion of the distal nickel-titanium wire 7120 beyond a distal end of the retainer 7130 is cut off. Further, the proximal nickel-titanium wire 7220 is fixed with a retainer 7230 (for example, a steel hoop), and an excess portion of the proximal nickel-titanium wire 7220 beyond a proximal end of the retainer 7230 is cut off to complete assembly.

Figure 35:
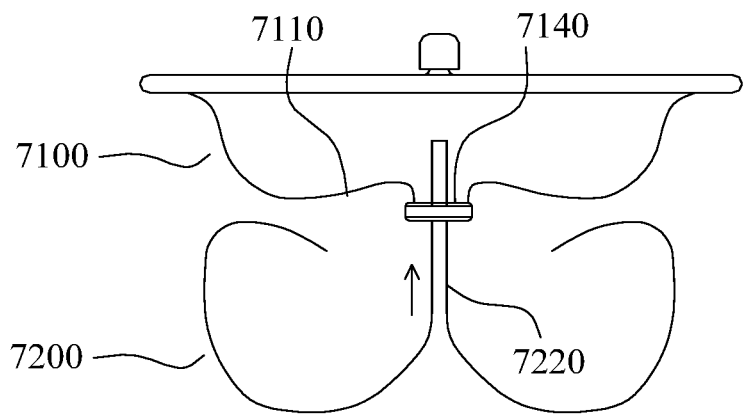
Figure 36:
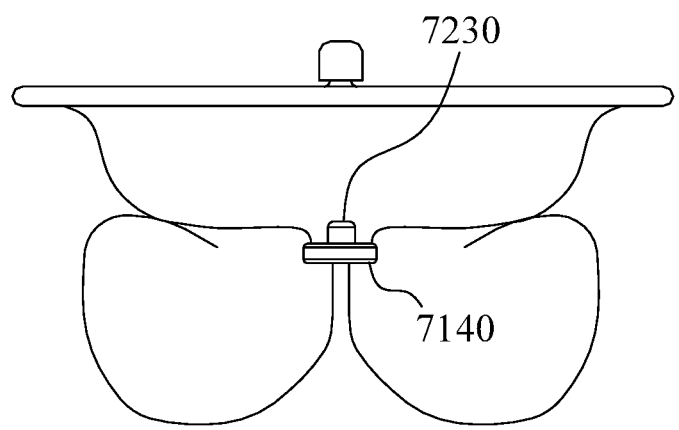

In another implementation, as illustrated in FIG. 35 and FIG. 36, the central part of the disc bottom 7110 is constricted and converged to form the connection part, and an end of the connection part of the anchoring portion 7200 is fixed with a connector 7140 (for example, a steel sleeve). The central part of the anchoring portion 7200 is wholly converged to form the proximal nickel-titanium wire 7220. The proximal nickel-titanium wire 7220 extends through a hollow portion of the connector 7140 and is tensioned against the anchoring portion 7200 to generate the pre-tightening force. When the anchoring portion 7200 and the sealing portion 7100 abut tightly against each other, and the middle part of the disc bottom 7110 is deformed to further protrude toward the anchoring portion 7200. The proximal nickel-titanium wire 7220 is fixed with a retainer 7230 (for example, a steel hoop), and an excess portion of the proximal nickel-titanium wire 7220 beyond a proximal end of the retainer 7230 is cut off to complete assembly.

Figure 37:
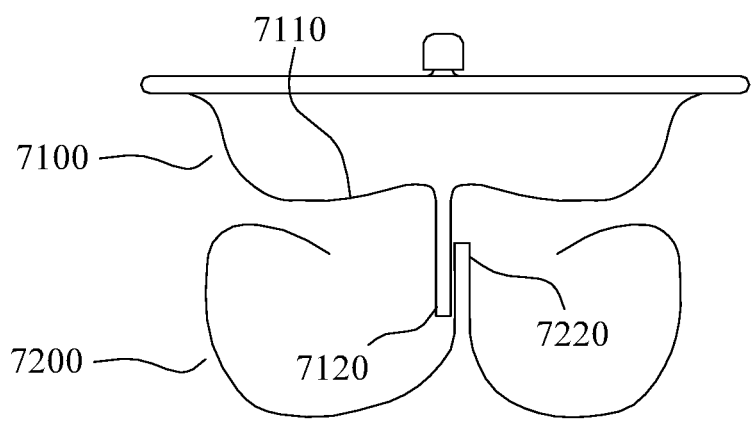
Figure 38:
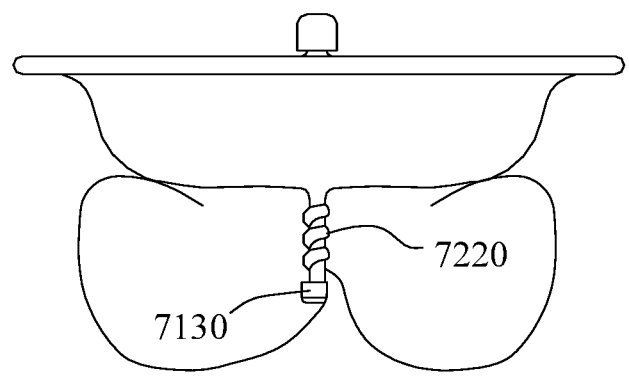

In another implementation, as illustrated in FIG. 37 and FIG. 38, the central part of the disc bottom 7110 is constricted and converged to form the connection part, that is, the central part of the disc bottom 7110 is converged to form the distal nickel-titanium wire 7120. The middle part of the anchoring portion 7200 is wholly converged to form a proximal nickel-titanium wire 7220.

The distal nickel-titanium wire 7120 and the proximal nickel-titanium wire 7220 are directly connected with each other, that is, a connector is omitted. As illustrated in FIG. 38, the proximal nickel-titanium wire 7220 is wound around an outer periphery of the distal nickel-titanium wire 7120. An end of the distal nickel-titanium wire 7120 may be provided with a retainer 7130 (for example, a steel hoop), and an end of the proximal nickel-titanium wire 7220 may be fixed at a disc bottom of the sealing portion 7100 by welding. In addition, the proximal nickel-titanium wire 7220 may be in a spiral shape and thermoformed in advance, and can be rewound around the outer periphery of the distal nickel-titanium wire 7120 after overcoming an elastic force to uncoil the proximal nickel-titanium wire 7220. Moreover, the distal nickel-titanium wire 7120 can also be interwound with the proximal nickel-titanium wire 7220 in a spiral manner.

Figure 39:
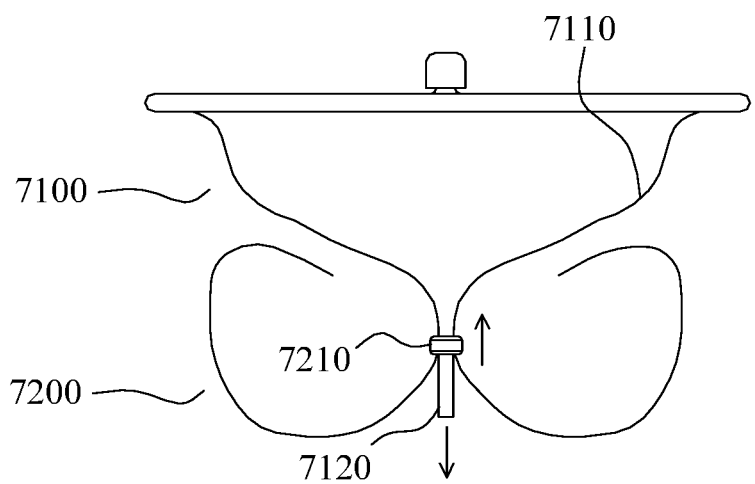
Figure 40:
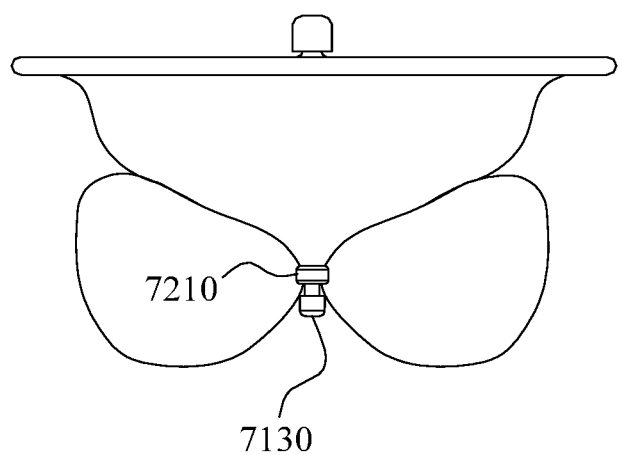

In another implementation, as illustrated in FIG. 39 and FIG. 40, the disc bottom 7110 is wholly converged to form a connection part, that is, the disc bottom 7110 is wholly converged to form the distal nickel-titanium wire 7120. The middle part of the anchoring portion 7200 is wholly converged to form a connection part, and an end of the connection part of the anchoring portion 7200 is fixed with a connector 7210 (for example, a steel sleeve). During assembling, the distal nickel-titanium wire 7120 extends through a hollow portion of the connector 7210 of the anchoring portion 7200 and is tensioned against the anchoring portion 7200 to generate the pre-tightening force. Finally, the distal nickel-titanium wire 7120 is fixed with the retainer 7130 (for example, a steel hoop), and an excess portion of the distal nickel-titanium wire 7120 beyond a distal end of the retainer 7130 is cut off to complete assembly.

The above embodiments are only specific embodiments of the present disclosure, but the present disclosure is not limited thereto. As will occur to those skilled in the art, the present disclosure is susceptible to various modifications and variations without departing from the spirit and principle of the present disclosure. It is obvious that these modifications and variations are within the scope of the present disclosure. In addition, although specific terms are adopted in the specification, these terms are merely for convenience of description and do not impose any particular limitation on the present disclosure.

What is claimed is:

1. A left atrial appendage occluder for improving sealing effect, comprising:
   a sealing portion; and
   an anchoring portion coupled to the sealing portion;
   wherein the sealing portion and the anchoring portion are abutted against each other, wherein peripheral regions of the anchoring portion and the sealing portion are abutted against each other, the peripheral regions of the anchoring portion and the sealing portion are regions around connection parts of the anchoring portion and the sealing portion.

2. The left atrial appendage occluder for improving sealing effect of claim 1, wherein the sealing portion comprises a disc surface facing away from the anchoring portion, a disc bottom facing the anchoring portion, and an intermediate part connecting the disc surface and the disc bottom, and wherein the disc bottom is planar, or a middle part of the disc bottom protrudes toward the anchoring portion, or the middle part of the disc bottom protrudes away from the anchoring portion.

3. The left atrial appendage occluder for improving sealing effect of claim 2, wherein the sealing portion is provided with a presetting state and an abutting state, and wherein in the presetting state the sealing portion is free from contact with the anchoring portion, and in the abutting state the sealing portion is in contact with the anchoring portion, and wherein a diameter of the disc bottom in the presetting state is larger than a diameter of the disc bottom in the abutting state.

4. The left atrial appendage occluder for improving sealing effect of claim 2, wherein the sealing portion is provided with a presetting state and an abutting state, and wherein in the presetting state the sealing portion is free from contact with the anchoring portion, and in the abutting state the sealing portion is in contact with the anchoring portion, and wherein at least one of the intermediate part and the disc bottom of the sealing portion in the abutting state has a deformation with respect to the presetting state.

5. The left atrial appendage occluder for improving sealing effect of claim 4, wherein the intermediate part of the sealing portion in the abutting state has a radially contracted deformation with respect to the presetting state, and the disc bottom of the sealing portion in the abutting state has a deformation protruding toward the anchoring portion axially with respect to the presetting state.

6. The left atrial appendage occluder for improving sealing effect of claim 1, wherein connection parts of the sealing portion and the anchoring portion are connected in a staggered manner.

7. The left atrial appendage occluder for improving sealing effect of claim 1, wherein:
the sealing portion and the anchoring portion are constricted and converged respectively, and the sealing portion and the anchoring portion are connected together via a connector;
the sealing portion comprises a bottom part facing the anchoring portion, and the bottom part of the sealing portion comprises a first converging part;
a middle part of the anchoring portion in a radial direction comprises a second converging part; and
the first converging part and the second converging part extend toward each other and are fixed together in a staggered manner.

8. The left atrial appendage occluder for improving sealing effect of claim 7, wherein the first converging part and the second converging part are arranged side-by-side in the staggered manner or are arranged in a nesting inside and outside in the staggered manner.

9. The left atrial appendage occluder for improving sealing effect of claim 7, wherein:
the anchoring portion extends from the connector away from the sealing portion to form an extending portion;
one side of the extending portion facing away from the connector is bent outward and turns back to the bottom part of the sealing portion to form a turning-back portion;
the turning-back portion bends inward and is constricted at the bottom part of the sealing portion to form a necked opening portion; and
the necked opening portion abuts against the bottom part of the sealing portion.

10. The left atrial appendage occluder for improving sealing effect of claim 9, wherein the necked opening portion is suspended above a periphery of the extending portion or connected to the extending portion, the extending portion is in a tapered shape, and an end of the extending portion having a larger diameter is disposed away from the connector and is provided with an opening.

11. The left atrial appendage occluder for improving sealing effect of claim 9, wherein the anchoring portion is provided with a presetting state and an abutting state, and wherein in the presetting state the anchoring portion is free from contact with the sealing portion, and wherein in the abutting state the anchoring portion is in contact with the sealing portion, and the connector is farther away from the sealing portion than the necked opening portion along an axial direction of the anchoring portion in the presetting state, and wherein the connector is flush with the necked opening portion or farther away from the sealing portion than the necked opening portion along the axial direction of the anchoring portion in the abutting state.

12. The left atrial appendage occluder for improving sealing effect of claim 7, wherein the connector comprises an outer ring and an inner ring nested within the outer ring, and wherein one of the first converging part and the second converging part extends through and is fixed in the inner ring, and the other one of the first converging part and the second converging part extends through and is fixed in a gap between the inner ring and the outer ring.

13. The left atrial appendage occluder for improving sealing effect of claim 7, wherein the connector comprises an outer ring and an inner ring nested within the outer ring, and wherein one of the first converging part and the second converging part extends through and is fixed in a gap between the inner ring and the outer ring, and the other one of the first converging part and the second converging part penetrates through the inner ring and is provided with a retainer abutted against the connector, the retainer being fixed to one end of the inner ring where the other one of the first converging part and the second converging part extends out.

14. The left atrial appendage occluder for improving sealing effect of claim 7, wherein the connector comprises a body having two passages arranged side by side, and wherein the first converging part and the second converging part extend through the two passages respectively and are provided with two retainers abutted against respective sides of the passages where the first converging part and the second converging part extend out correspondingly.

15. The left atrial appendage occluder for improving sealing effect of claim 1, wherein the sealing portion is a sealing disc and is provided with a presetting state and an abutting state, and wherein in the presetting state the sealing portion is free from contact with the anchoring portion, and wherein in the abutting state the sealing portion is in contact with the anchoring portion, and a middle part of a disc bottom of the sealing disc in the abutting state is deformed facing axially toward the anchoring portion with respect to the presetting state.

16. The left atrial appendage occluder for improving sealing effect of claim 1, wherein:
the sealing portion and the anchoring portion are formed individually and abut against each other during an assembling process; and
after thermoforming the sealing portion and the anchoring portion are assembled together, and wherein the sealing portion and the anchoring portion are in a first state in an initial contact with each other during assembly, and wherein connection parts of the sealing portion and the anchoring portion are in a second state after axially moving a predetermined distance toward each other.

17. The left atrial appendage occluder for improving sealing effect of claim 16, wherein the connection parts of the sealing portion and the anchoring portion are respectively disposed at middle parts of the sealing portion and the anchoring portion in a radial direction, and wherein in the first state the sealing portion and the anchoring portion are in contact with each other at peripheral regions around the connection parts respectively.

18. The left atrial appendage occluder for improving sealing effect of claim 17, wherein in the second state a part of the sealing portion connected with the anchoring portion moved towards the anchoring portion with respect to the first state, and the predetermined distance is defined according to one of:
an axial force of the connection parts between the sealing portion and the anchoring portion;
a pressing force at contacting parts of the sealing portion and the anchoring portion; and
a deformation of the part of the sealing portion connected with the anchoring portion.

19. The left atrial appendage occluder for improving sealing effect of claim 18, wherein the deformation is an axial displacement of a predetermined part of the sealing portion, or an angle between the predetermined part of the sealing portion and an axis of the sealing portion.

20. A method for manufacturing a left atrial appendage occluder for improving sealing effect of claim 1, comprising:

performing thermoforming on the sealing portion and the anchoring portion;

when assembling the sealing portion with the anchoring portion, causing the sealing portion and the anchoring portion to move toward each other to reach a first state, wherein in the first state the sealing portion and the anchoring portion are in initial contact with each other;

causing the sealing portion and the anchoring portion to move axially toward each other a predetermined distance to reach a second state; and fixing connection parts of the sealing portion and the anchoring portion together, wherein the connection parts are maintained in the second state to complete assembly.

* * * * *